United States Patent
Olmeijer et al.

(10) Patent No.: US 11,999,884 B2
(45) Date of Patent: Jun. 4, 2024

(54) THERMALLY STABLE POLYTHIOL LIGANDS WITH PENDANT SOLUBILIZING MOIETIES

(71) Applicant: Shoei Chemical Inc., Tokyo (JP)

(72) Inventors: David Olmeijer, San Francisco, CA (US); Ravisubhash Tangirala, Fremont, CA (US); Austin Smith, Redwood City, CA (US)

(73) Assignee: SHOEI CHEMICAL INC., Tokyo (JP)

(*) Notice: Subject to any disclaimer, the term of this patent is extended or adjusted under 35 U.S.C. 154(b) by 101 days.

(21) Appl. No.: 17/487,148

(22) Filed: Sep. 28, 2021

(65) Prior Publication Data

US 2022/0098475 A1 Mar. 31, 2022

Related U.S. Application Data

(60) Provisional application No. 63/084,299, filed on Sep. 28, 2020.

(51) Int. Cl.
*C09K 11/02* (2006.01)
*B82Y 20/00* (2011.01)
(Continued)

(52) U.S. Cl.
CPC .......... *C09K 11/025* (2013.01); *C07C 319/18* (2013.01); *C09K 11/565* (2013.01);
(Continued)

(58) Field of Classification Search
CPC . C09K 11/025; C09K 11/883; C09K 11/7492; C09K 11/565; B82Y 20/00; B82Y 40/00
See application file for complete search history.

(56) References Cited

U.S. PATENT DOCUMENTS

| 5,505,928 A | 4/1996 | Alivisatos et al. |
| 6,207,229 B1 | 3/2001 | Bawendi et al. |

(Continued)

FOREIGN PATENT DOCUMENTS

| EP | 3444317 A1 | 2/2019 |
| WO | WO-2016023821 A1 | 2/2016 |

(Continued)

OTHER PUBLICATIONS

Mei, B.C., et al., "Polyethylene glycol-based bidentate ligands to enhance quantum dot and gold nanoparticle stability in biological media," Nature Protocols 4:412-423, Springer, Netherlands (Mar. 2009).

(Continued)

*Primary Examiner* — C Melissa Koslow
(74) *Attorney, Agent, or Firm* — Alleman Hall & Tuttle LLP

(57) ABSTRACT

The present invention provides nanostructure compositions and methods of producing nanostructure compositions. The nanostructure compositions comprise a population of nanostructures comprising polythiol ligands with pendant moieties. The polythiol ligand with pendant moieties increase the solubility of the nanostructures in solvents and resins. The present invention also provides nanostructure films comprising the nanostructure compositions and methods of making nanostructure films using the nanostructure compositions.

16 Claims, 2 Drawing Sheets

(51) Int. Cl.
    *B82Y 40/00* (2011.01)
    *C07C 319/18* (2006.01)
    *C07C 323/22* (2006.01)
    *C09K 11/56* (2006.01)
    *C09K 11/74* (2006.01)
    *C09K 11/88* (2006.01)

(52) U.S. Cl.
    CPC ........ *C09K 11/7492* (2013.01); *C09K 11/883* (2013.01); *B82Y 20/00* (2013.01); *B82Y 40/00* (2013.01); *C07C 323/22* (2013.01)

(56) References Cited

U.S. PATENT DOCUMENTS

| | | |
|---|---|---|
| 6,225,198 B1 | 5/2001 | Alivisatos et al. |
| 6,306,736 B1 | 10/2001 | Alivisatos et al. |
| 6,322,901 B1 | 11/2001 | Bawendi et al. |
| 6,576,291 B2 | 6/2003 | Bawendi et al. |
| 6,607,829 B1 | 8/2003 | Bawendi et al. |
| 6,788,453 B2 | 9/2004 | Banin et al. |
| 6,821,337 B2 | 11/2004 | Bawendi et al. |
| 6,861,155 B2 | 3/2005 | Bawendi et al. |
| 7,060,243 B2 | 6/2006 | Bawendi et al. |
| 7,125,605 B2 | 10/2006 | Bawendi et al. |
| 7,138,098 B2 | 11/2006 | Bawendi et al. |
| 7,374,824 B2 | 5/2008 | Bawendi et al. |
| 7,557,028 B1 | 7/2009 | Scher et al. |
| 7,566,476 B2 | 7/2009 | Bawendi et al. |
| 7,588,828 B2 | 9/2009 | Mushtaq et al. |
| 7,645,397 B2 | 1/2010 | Parce et al. |
| 8,062,967 B1 | 11/2011 | Scher et al. |
| 8,101,234 B2 | 1/2012 | Bawendi et al. |
| 8,158,193 B2 | 4/2012 | Bawendi et al. |
| 8,282,412 B1 | 10/2012 | Yaguchi et al. |
| 11,021,651 B2 | 6/2021 | Plante et al. |
| 11,041,071 B2 | 6/2021 | Tangirala et al. |
| 2011/0262752 A1 | 10/2011 | Bawendi et al. |
| 2011/0263062 A1 | 10/2011 | Bawendi et al. |
| 2015/0236195 A1 | 8/2015 | Guo et al. |
| 2017/0152437 A1 | 6/2017 | Cano et al. |
| 2018/0057658 A1* | 3/2018 | Qiu .................. C09K 11/883 |
| 2018/0079868 A1 | 3/2018 | Yamada et al. |
| 2018/0346718 A1* | 12/2018 | Goethel ................ C08G 18/00 |
| 2020/0190400 A1 | 6/2020 | Hirayama et al. |

FOREIGN PATENT DOCUMENTS

| | | |
|---|---|---|
| WO | WO-2019084119 A1 | 5/2019 |
| WO | WO-2022067222 A1 | 3/2022 |

OTHER PUBLICATIONS

International Search Report and Written Opinion for International Application No. PCT/US2021/052280, European Patent Office, Netherlands, dated Jan. 4, 2022, 8 pages.

Nguyen, L.-T. T, et al., "Kinetic comparison of 13 homogeneous thiol-X reactions," Polym. Chem. 4:5527-5536, Royal Society of Chemistry, United States (Jan. 2013).

Owen, J.S., et al., "Reaction chemistry and ligand exchange at cadmium-selenide nanocrystal surfaces," J Am. Chem. Soc. 130(37):12279-12281, American Chemical Society, United States (Sep. 2008).

Wells, R. et al., "The use of tris(trimethylsilyl)arsine to prepare gallium arsenide and indium arsenide," Chemistry of Materials Technical Report No. DU/DC/TR-10, Oct. 3, 1988, 13 pages.

Guzelian, A. et al., "Colloidal chemical synthesis and characterization of InAs nanocrystal quantum dots," Applied Physics Letters, vol. 69, No. 10, Sep. 2, 1996, 3 pages.

Xie, R. et al., "Colloidal InP nanocrystals as efficient emitters covering blue to near-infrared," Journal of the American Chemical Society, vol. 129, No. 50, Nov. 23, 2007, 2 pages.

Micic, O. et al., "Core-shell quantum dots of lattice-matched ZnCdSe2 shells on InP cores: Experiment and theory," The Journal of Physical Chemistry B, vol. 104, No. 51, Dec. 28, 2000, 8 pages.

Liu, Z. et al., "Coreduction colloidal synthesis of III-V nanocrystals: The case of InP," Angewandte Chemie International Edition, vol. 47, No. 19, Apr. 21, 2008, 3 pages.

Li, L. et al., "Economic synthesis of high quality InP nanocrystals using calcium phosphide as the phosphorus precursor," Chemistry of Materials, vol. 20, No. 8, Mar. 20, 2008, 3 pages.

Battaglia, D. et al., "Formation of high quality InP and InAs nanocrystals in a noncoordinating solvent," Nano Letters, vol. 2, No. 9, Aug. 15, 2002, 4 pages.

Park, J. et al., "Highly luminescent InP/GaP/ZnS QDs emitting in the entire color range via a heating up process," Scientific Reports, vol. 6., No. 30094, Jul. 20, 2016, 6 pages.

Nann, T. et al., "Water splitting by visible light: A nanophotocathode for hydrogen production," Angewandte Chemie International Edition, vol. 49, No. 9, Feb. 22, 2010, 4 pages.

Borchert, H. et al., "Investigation of ZnS passivated InP nanocrystals by XPS," Nano Letters vol. 2, No. 2, Dec. 14, 2001, 4 pages.

Li, L. et al., "One-pot synthesis of highly luminescent InP/ZnS nanocrystals without precursor injection," Journal of the American Chemical Society, vol. 130, No. 35, Aug. 8, 2008, 2 pages.

Hussain, S. et al., "One-pot fabrication of high-quality InP/ZnS (core/shell) quantum dots and their application to cellular imaging," ChemPhysChem, vol. 10, No. 9-10, Jun. 9, 2009, 5 pages.

Xu, S. et al., "Rapid synthesis of high-quality InP nanocrystals," Journal of the American Chemical Society, vol. 128, No. 4, Jan. 6, 2007, 2 pages.

Micic, O. et al., "Size-dependent spectroscopy of InP quantum dots," The Journal of Physical Chemistry B, vol. 101, No. 25, Jun. 19, 1997, 9 pages.

Haubold, S. et al., "Strongly luminescent InP/ZnS core-shell nanoparticles," ChemPhysChem, vol. 2, No. 5, May 15, 2001, 4 pages.

Cros-Gagneux, A. et al., "Surface chemistry of InP quantum dots: A comprehensive study," Journal of the American Chemical Society, vol. 132, No. 51, Dec. 2, 2010, 11 pages.

Micic, O. et al., "Synthesis and characterization of InP, GaP, and GaInP2 quantum dots," The Journal of Physical Chemistry, vol. 99, No. 19, May 1, 1995, 6 pages.

Guzelian, A. et al., "Synthesis of size-selected, surface-passivated InP nanocrystals," The Journal of Physical Chemistry, vol. 100, No. 17, Apr. 25, 1996, 8 pages.

Lucey, D. et al., "Monodispersed InP quantum dots prepared by colloidal chemistry in a non-coordinating solvent," Chemistry of Materials, vol. 17, No. 14, Jun. 15, 2005, 9 pages.

Lim, J. et al., "InP@ZnSeS, core@composition gradient shell quantum dots with enhanced stability," Chemistry of Materials, vol. 23, No. 20, Oct. 25, 2011, 6 pages.

Zan, F. et al., "Experimental studies on blinking behavior of single InP/ZnS quantum dots: Effects of synthetic conditions and UV irradiation," The Journal of Physical Chemistry C, vol. 116, No. 6, Jan. 19, 2012, 7 pages.

\* cited by examiner

THERMALLY STABLE POLYTHIOL LIGANDS WITH PENDANT SOLUBILIZING MOIETIES

FIELD OF THE INVENTION

The present invention provides nanostructure compositions and methods of producing nanostructure compositions. The nanostructure compositions comprise a population of nanostructures comprising polythiol ligands with pendant moieties. The polythiol ligand with pendant moieties increase the solubility of the nanostructures in solvents and resins. The present invention also provides nanostructure films comprising the nanostructure compositions and methods of making nanostructure films using the nanostructure compositions.

BACKGROUND OF THE INVENTION

Synthetic methods that enable the preparation of quantum dots with accurate control of their properties afford nanocrystals whose surface is coated with a layer of highly hydrophobic molecular ligands. These quantum dots are therefore (moderately) soluble only in polar organic solvents such as toluene, hexane, or chloroform. Several applications of quantum dots, however require water soluble nanocrystals. This objective can be reached with the functionalization of the nanocrystals' surface by appropriate molecular ligands. For example, a series of poly(ethylene glycol)-based bidentate ligands were produced that showed a strong interaction with CdSe/ZnS (core/shell) quantum dots and gold nanoparticles and promoted their dispersion in aqueous solutions. Bing, C. M., et al., *Nature Protocols* 4:412-423 (2009). However, Owen, J. S., et al., *J. Am. Chem. Soc.* 130(37):12279-12281 (2008) found that ligand exchange of octadecylphosphonate ligands with —S—$(CH_2CH_2O)_4OCH_3$ resulted in the binding of the thiol to the nanoparticle surface but caused quenching of the nanoparticle fluorescence.

Organic molecules bind to the inorganic surfaces of quantum dots providing both colloidal stability and terminating the crystalline lattice of the material reducing the number of surface trap states caused by dangling bonds. As-synthesized quantum dots produced from the reaction of metal carboxylates (i.e, metal oleates, stearates, laurates, etc.) with chalcogenide precursors result in the formation of a metal-rich quantum dot surface terminated primarily by metal carboxylate ligands. Additionally, for reactions utilizing primary alkyl thiols as the sulfur precursor, unreacted thiol species can also serve as ligands.

The native ligand set (including metal carboxylates, metal thiolates, and thiols) of most quantum dots are hydrophobic and thus are not inherently soluble in a wide range of organic media. Generally, the surface ligands need to be replaced to confer solubility in these media. Ligand exchange procedures have been performed using either a polyethylene glycol (PEG) based polymeric ligand functionalized with an amine or a carboxylic acid. For some quantum dots, the PEG-based polymeric ligands with amine functional groups cannot be used since exposure to primary amines results in severe quenching of the photoluminescence quantum yield. Ligand exchange with carboxylic acid functionalized polymeric ligands results in nominal solubility in various resin formulations, however challenges remain regarding broadening of the full width at half-maximum (FWHM) upon ligand exchange, the reliability of the QDEF product under high-flux testing conditions, and early-time variations in the emission power (i.e, burn in). A potential cause for these concerns is that exposure to thiol functional groups present in many resin formulations can result in the displacement of carboxylate groups and disruption of the quantum dot colloidal stability.

Metal thiolate bonds have been found to be stronger than both metal carboxylate and metal phosphonate bonds and exposure to thiols or the corresponding deprotonated thiolate results in displacement of the carboxylate ligand from the surface as a carboxylic acid. Furthermore, thiols can also bind to the surface of nanocrystals as neutral L-type ligands occupying sites left open by the surface packing of metal carboxylate ligands. Either mechanism—displacement of the polymeric carboxylic ligands or the aggregation of multiple quantum dots by multifunctional thiol molecules present in the resin formulations—can result in undesirable deterioration of the quantum dot optical properties.

A need exists to prepare nanostructure compositions and/or resin mixes that have improved stability and result in improved optical properties when used to prepare a nanostructure film.

BRIEF SUMMARY OF THE INVENTION

Provided is a nanostructure composition comprising:
(a) a nanostructure; and
(b) polythiol ligands dispersed on the surface of the nanostructure, the polythiol ligands having the formula I:

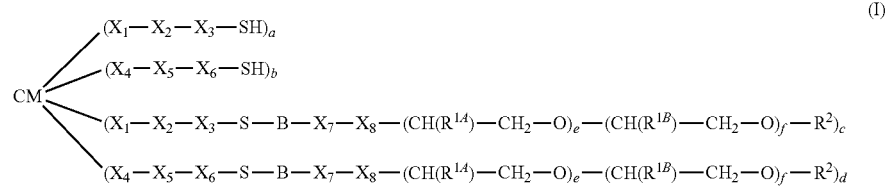

wherein:
CM is a central moiety;
$X_1$ is a bond, —C(=O)—, a $C_{1-10}$ alkylene, or a $C_{2-10}$ heteroalkylene;
$X_2$ is a bond, —C(=O)—, a $C_{1-10}$ alkylene, or a $C_{2-10}$ heteroalkylene;
$X_3$ is a bond, —C(=O)—, a $C_{1-10}$ alkylene, or a $C_{2-10}$ heteroalkylene;
$X_4$ is a bond, —C(=O)—, a $C_{1-10}$ alkylene, or a $C_{2-10}$ heteroalkylene;
$X_5$ is a bond, —C(=O)—, a $C_{1-10}$ alkylene, or a $C_{2-10}$ heteroalkylene;
$X_6$ is a bond, —C(=O)—, a $C_{1-10}$ alkylene, or a $C_{2-10}$ heteroalkylene;

B is —CH₂—CH₂—C(=O)—O—, —CH₂—C(CH₃)₂—C(=O)—O—, —CH₂—CH(CH₃)—C(=O)—NH—, —C(=O)—NH—, —CH₂—CH₂—, or —CH₂—CH(OH)—CH₂—O—;
$X_7$ is a bond or $C_{1-12}$ alkylene;
$X_8$ is a bond, —O—, —C(=O)—O—, or —C(=O)—N—;
$R^{1A}$ and $R^{1B}$ independently are H or $C_{1-20}$ alkyl;
$R^2$ is $C_{1-20}$ alkyl or $C_{1-20}$ alkoxy;
a is 2 to 10;
b is 0 to 10;
c is 2 to 10;
d is 0 to 10;
e is 1 to 100; and
f is 0 to 100;
wherein a+b+c+d comprises a value within a range of 4 to 40.

In some embodiments, the polythiol ligands have formula II:

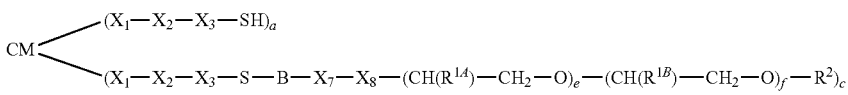

(II)

wherein:
CM is a central moiety;
$X_1$ is a bond, —C(=O)—, a $C_{1-10}$ alkylene, or a $C_{2-10}$ heteroalkylene;
$X_2$ is a bond, —C(=O)—, a $C_{1-10}$ alkylene, or a $C_{2-10}$ heteroalkylene;
$X_3$ is a bond, —C(=O)—, a $C_{1-10}$ alkylene, or a $C_{2-10}$ heteroalkylene;
B is —CH₂—CH₂—C(=O)—O—, —CH₂—C(CH₃)₂—C(=O)—O—, —CH₂—CH(CH₃)—C(=O)—NH—, —C(=O)—NH—, —CH₂—CH₂—, or —CH₂—CH(OH)—CH₂—O—;
$X_7$ is a bond or $C_{1-12}$ alkylene;
$X_8$ is a bond, —O—, —C(=O)—O—, or —C(=O)—N—;
$R^{1A}$ and $R^{1B}$ independently are H or $C_{1-20}$ alkylene;
$R^2$ is $C_{1-20}$ alkylene or $C_{1-20}$ alkoxy;
a is 2 to 10;
c is 2 to 10;
e is 1 to 100; and
f is 0 to 100;
wherein a +c≥4 and ≤20.

In some embodiments, CM is selected from the group consisting of an alkane, a 1,3,5-triazine, a pentaerythritol, a 1,3,5-triazine-2,4,6-trione, a trimethylolpropane, and a (propane-2,2-diylbis(4,1-phenylene))bis(λ'-oxy).

In some embodiments, the nanostructure comprises a core selected from the group consisting of InP, InZnP, InGaP, CdSe, CdS, CdSSe, CdZnSe, CdZnS, ZnSe, ZnSSe, InAs, InGaAs, and InAsP.

In some embodiments, the nanostructure comprises at least one shell.
In some embodiments, $X_1$, $X_2$, and $X_3$ are a bond.
In some embodiments, $X_1$ is —C(=O)—, $X_2$ is a $C_{1-10}$ alkylene, and $X_3$ is a bond.
In some embodiments, $X_1$ is $C_{2-10}$ heteroalkylene, $X_2$ is —C(=O)—, and $X_3$ is a $C_{1-10}$ alkylene.
In some embodiments, $X_1$ is a substituted $C_{2-10}$ heteroalkylene, $X_2$ is a bond, and $X_3$ is a bond.
In some embodiments, B is —CH₂—CH₂—.
In some embodiments, $X_7$ is a $C_{1-10}$ alkylene and $X_8$ is —C(=O)—O—.
In some embodiments, $R^{1A}$ is H, e is 1 to 100, a is 2, and c is 2.

In some embodiments, the nanostructure composition is soluble in a solvent selected from the group consisting of water, methanol, ethanol, acetone, methyl ethyl ketone, isopropanol, n-propanol, acetonitrile, dimethyl sulfoxide, dimethyl formamide, ethylene glycol, diethylene glycol, benzonitrile, cyclohexane, chloroform, ethyl acetate, propylene glycol methyl acetate, and dichloromethane.

Also provided is a method of replacing a first ligand on a nanostructure with a second ligand comprising admixing a reaction mixture comprising a population of nanostructures having a first ligand non-covalently bound to the nanostructure and a second ligand which is a polythiol ligand, such that the second ligand displaces the first ligand and becomes non-covalently bound to the nanostructure, wherein the polythiol ligand has formula I:

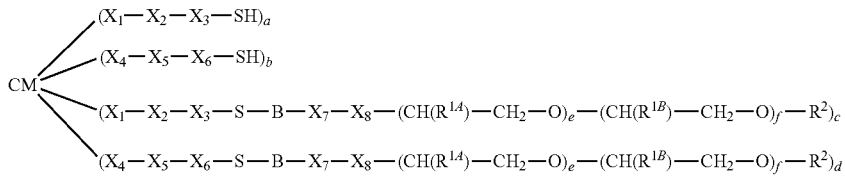

(I)

wherein:
CM is a central moiety;
$X_1$ is a bond, —C(=O)—, a $C_{1-10}$ alkylene, or a $C_{2-10}$ heteroalkylene;
$X_2$ is a bond, —C(=O)—, a $C_{1-10}$ alkylene, or a $C_{2-10}$ heteroalkylene;
$X_3$ is a bond, —C(=O)—, a $C_{1-10}$ alkylene, or a $C_{2-10}$ heteroalkylene;
$X_4$ is a bond, —C(=O)—, a $C_{1-10}$ alkylene, or a $C_{2-10}$ heteroalkylene;
$X_5$ is a bond, —C(=O)—, a $C_{1-10}$ alkylene, or a $C_{2-10}$ heteroalkylene;
$X_6$ is a bond, —C(=O)—, a $C_{1-10}$ alkylene, or a $C_{2-10}$ heteroalkylene;
B is —CH₂—CH₂—C(=O)—O—, —CH₂—C(CH₃)₂—C(=O)—O—, —CH₂—CH(CH₃)—C (=O)—NH—, —C(=O)—NH—, —CH$_2$—CH$_2$—, or —CH$_2$—CH(OH)—CH$_2$—O—;

$X_7$ is a bond or C$_{1-12}$ alkylene;

$X_8$ is a bond, —O—, —C(=O)—O—, or —C(=O)—N—;

$R^{1A}$ and $R^{1B}$ independently are H or C$_{1-20}$ alkyl;

$R^2$ is C$_{1-20}$ alkyl or C$_{1-20}$ alkoxy.

a is 2 to 10;
b is 0 to 10;
c is 2 to 10;
d is 0 to 10;
e is 1 to 100; and
f is 0 to 100;

wherein a+b+c+d comprises a value within a range of 4 to 40.

In some embodiments, CM is selected from the group consisting of an alkane, a 1,3,5-triazine, a pentaerythritol, a 1,3,5-triazine-2,4,6-trione, a trimethylolpropane, and a (propane-2,2-diylbis(4,1-phenylene))bis(λ'-oxy).

In some embodiments, the nanostructure comprises a core selected from the group consisting of InP, InZnP, InGaP, CdSe, CdS, CdSSe, CdZnSe, CdZnS, ZnSe, ZnSSe, InAs, InGaAs, and InAsP.

Also provided is a nanostructure film layer comprising:
(a) a nanostructure;
(b) polythiol ligands dispersed on the surface of the nanostructure, the polythiol ligands having the formula I:

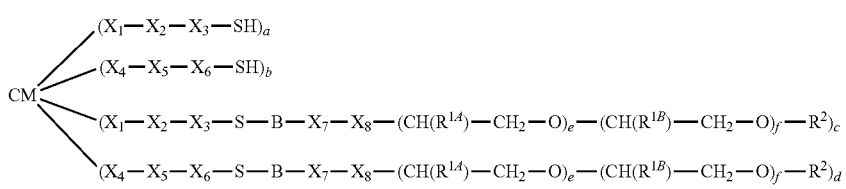

(I)

wherein:
CM is a central moiety;
$X_1$ is a bond, —C(=O)—, a C$_{1-10}$ alkylene, or a C$_{2-10}$ heteroalkylene;
$X_2$ is a bond, —C(=O)—, a C$_{1-10}$ alkylene, or a C$_{2-10}$ heteroalkylene;
$X_3$ is a bond, —C(=O)—, a C$_{1-10}$ alkylene, or a C$_{2-10}$ heteroalkylene;
$X_4$ is a bond, —C(=O)—, a C$_{1-10}$ alkylene, or a C$_{2-10}$ heteroalkylene;
$X_5$ is a bond, —C(=O)—, a C$_{1-10}$ alkylene, or a C$_{2-10}$ heteroalkylene;
$X_6$ is a bond, —C(=O)—, a C$_{1-10}$ alkylene, or a C$_{2-10}$ heteroalkylene;
B is —CH$_2$—CH$_2$—C(=O)—O—, —CH$_2$—C(CH$_3$)$_2$—C(=O)—O—, —CH$_2$—CH(CH$_3$)—C(=O)—NH—, —C(=O)—NH—, —CH$_2$—CH$_2$—, or —CH$_2$—CH(OH)—CH$_2$—O—;
$X_7$ is a bond or C$_{1-12}$ alkylene;
$X_8$ is a bond, —O—, —C(=O)—O—, or —C(=O)—N—;
$R^{1A}$ and $R^{1B}$ independently are H or C$_{1-20}$ alkyl;
$R^2$ is C$_{1-20}$ alkyl or C$_{1-20}$ alkoxy.
a is 2 to 10;
b is 0 to 10;
c is 2 to 10;
d is 0 to 10;
e is 1 to 100; and
f is 0 to 100;
wherein a+b+c+comprises a value within a range of 4 to 40; and
(c) at least one organic resin.

In some embodiments, CM is selected from the group consisting of an alkane, a 1,3,5-triazine, a pentaerythritol, a 1,3,5-triazine-2,4,6-trione, a trimethylolpropane, and a (propane-2,2-diylbis(4,1-phenylene))bis(λ'-oxy).

In some embodiments, the nanostructure film layer displays a light conversion efficiency between about 20% and about 40%.

Also provided is a method of preparing the polythiol ligands described above comprising reacting a polythiol of formula III:

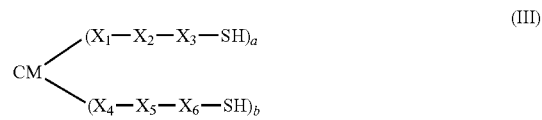

(III)

wherein:
CM is a central moiety;
$X_1$ is a bond, —C(=O)—, a C$_{1-10}$ alkylene, or a C$_{2-10}$ heteroalkylene;
$X_2$ is a bond, —C(=O)—, a C$_{1-10}$ alkylene, or a C$_{2-10}$ heteroalkylene;
$X_3$ is a bond, —C(=O)—, a C$_{1-10}$ alkylene, or a C$_{2-10}$ heteroalkylene;
$X_4$ is a bond, —C(=O)—, a C$_{1-10}$ alkylene, or a C$_{2-10}$ heteroalkylene;
$X_5$ is a bond, —C(=O)—, a C$_{1-10}$ alkylene, or a C$_{2-10}$ heteroalkylene;
$X_6$ is a bond, —C(=O)—, a C$_{1-10}$ alkylene, or a C$_{2-10}$ heteroalkylene;
a is 2 to 10; and
b is 0 to 10;
and wherein a+b≥3;
with a poly(alkylene oxide) of formula V:

(V)

wherein:
FG is an acrylate group, a methacrylate group, an acrylamide group,
an isocyanate group, an alkene group, or a glycidyl ether group;
$X_7$ is a bond or C$_{1-12}$ alkylene;

$X_8$ is a bond, —O—, —C(=O)—O—, or —C(=O)—N—;

$R^{1A}$ and $R^{1B}$ independently are H or $C_{1-20}$ alkyl;

e is 1 to 100;

f is 0 to 100; and $R^2$ is $C_{1-20}$ alkyl or $C_{1-20}$ alkoxy.

BRIEF DESCRIPTION OF THE DRAWINGS

The accompanying drawing, which is incorporated herein and form a part of the specification, illustrate the present invention and, together with the description, further serve to explain the principles of the invention and to enable a person skilled in the art in to make and use the invention.

DETAILED DESCRIPTION OF THE INVENTION

Figure 1:
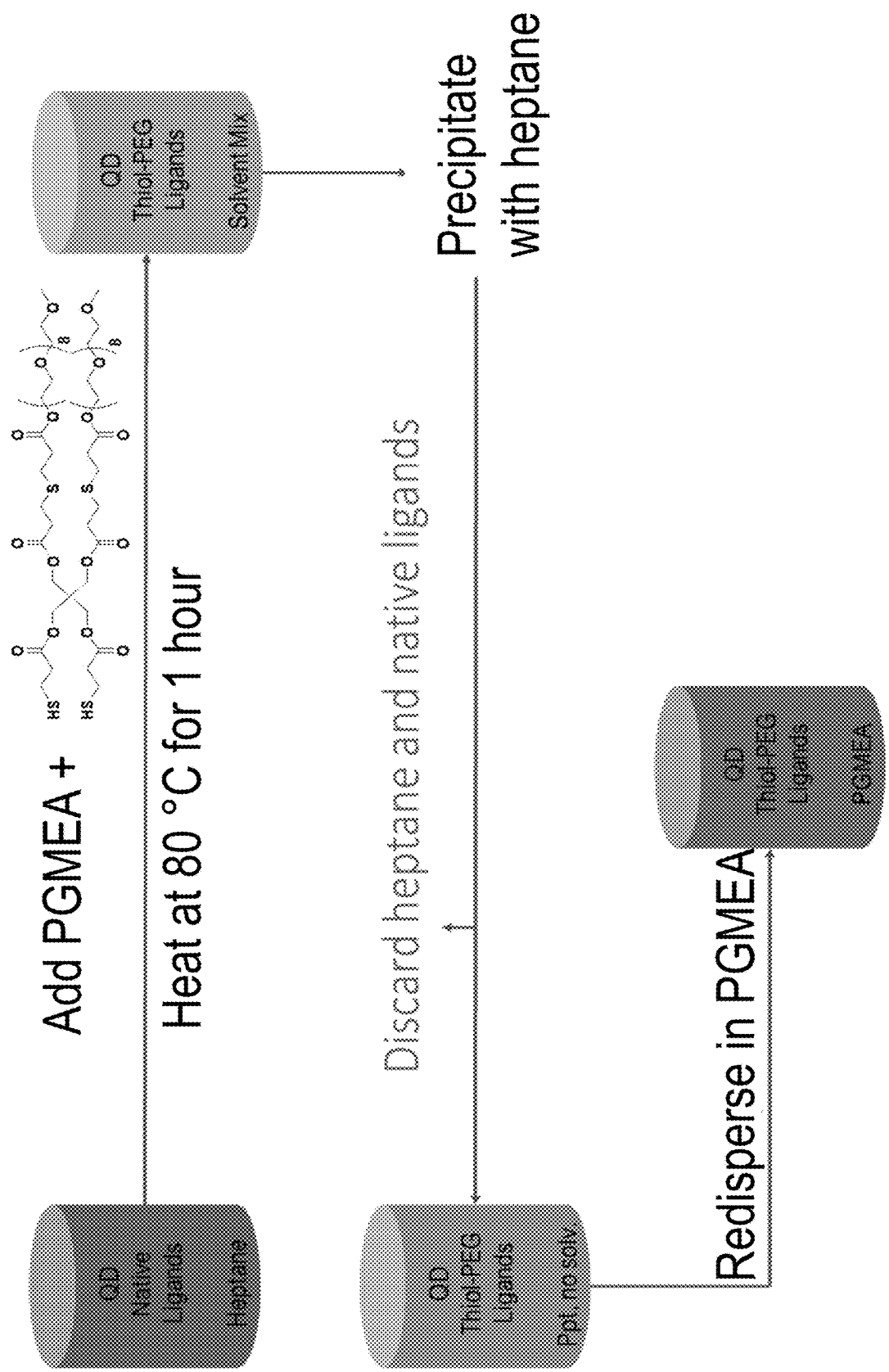
FIG. 1 is flow chart showing the ligand exchange procedure of Example 2. In the first step, PETMP-PEG-480 ligands and quantum dots containing native ligands are added to propylene glycol methyl ether acetate which is then heated to 80° C. for 1 hour. In the second step, the solution is cooled to room temperature and then heptane is added to precipitate the quantum dots. In the third step, the precipitate is centrifuged to provide a quantum dot pellet which can be redispersed in propylene glycol methyl ether acetate.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in practice for testing, the preferred materials and methods are described herein. Accordingly, the terminology used herein is for the purpose of describing particular embodiments only, and is not intended to be limiting.

As used in this specification and the appended claims, the singular forms "a," "an," and "the" include plural referents unless the context clearly dictates otherwise. Thus, for example, reference to "a nanostructure" includes a plurality of such nanostructures, and the like.

The term "about" as used herein indicates the value of a given quantity varies by 10% of the value. For example, "about 100 nm" encompasses a range of sizes from 90 nm to 110 nm, inclusive.

A "nanostructure" is a structure having at least one region or characteristic dimension with a dimension of less than about 500 nm. In some embodiments, the nanostructure has a dimension of less than about 200 nm, less than about 100 nm, less than about 50 nm, less than about 20 nm, or less than about 10 nm. Typically, the region or characteristic dimension will be along the smallest axis of the structure. Examples of such structures include nanowires, nanorods, nanotubes, branched nanostructures, nanotetrapods, tripods, bipods, nanocrystals, nanodots, quantum dots, nanoparticles, and the like. Nanostructures can be, e.g., substantially crystalline, substantially monocrystalline, polycrystalline, amorphous, or a combination thereof. In some embodiments, each of the three dimensions of the nanostructure has a dimension of less than about 500 nm, less than about 200 nm, less than about 100 nm, less than about 50 nm, less than about 20 nm, or less than about 10 nm.

The term "heterostructure" when used with reference to nanostructures refers to nanostructures characterized by at least two different and/or distinguishable material types. Typically, one region of the nanostructure comprises a first material type, while a second region of the nanostructure comprises a second material type. In certain embodiments, the nanostructure comprises a core of a first material and at least one shell of a second (or third etc.) material, where the different material types are distributed radially about the long axis of a nanowire, a long axis of an arm of a branched nanowire, or the center of a nanocrystal, for example. A shell can but need not completely cover the adjacent materials to be considered a shell or for the nanostructure to be considered a heterostructure; for example, a nanocrystal characterized by a core of one material covered with small islands of a second material is a heterostructure. In other embodiments, the different material types are distributed at different locations within the nanostructure; e.g., along the major (long) axis of a nanowire or along a long axis of arm of a branched nanowire. Different regions within a heterostructure can comprise entirely different materials, or the different regions can comprise a base material (e.g., silicon) having different dopants or different concentrations of the same dopant.

As used herein, the "diameter" of a nanostructure refers to the diameter of a cross-section normal to a first axis of the nanostructure, where the first axis has the greatest difference in length with respect to the second and third axes (the second and third axes are the two axes whose lengths most nearly equal each other). The first axis is not necessarily the longest axis of the nanostructure; e.g., for a disk-shaped nanostructure, the cross-section would be a substantially circular cross-section normal to the short longitudinal axis of the disk. Where the cross-section is not circular, the diameter is the average of the major and minor axes of that cross-section. For an elongated or high aspect ratio nanostructure, such as a nanowire, the diameter is measured across a cross-section perpendicular to the longest axis of the nanowire. For a spherical nanostructure, the diameter is measured from one side to the other through the center of the sphere.

The terms "crystalline" or "substantially crystalline," when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating can but need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

A "nanocrystal" is a nanostructure that is substantially monocrystalline. A nanocrystal thus has at least one region or characteristic dimension with a dimension of less than about 500 nm. In some embodiments, the nanocrystal has a dimension of less than about 200 nm, less than about 100 nm, less than about 50 nm, less than about 20 nm, or less than about 10 nm. The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. In some embodiments, each of the three dimensions of the nanocrystal has a dimension of less than about 500 nm, less than about 200 nm, less than about 100 nm, less than about 50 nm, less than about 20 nm, or less than about 10 nm.

The term "quantum dot" (or "dot") refers to a nanocrystal that exhibits quantum confinement or exciton confinement. Quantum dots can be substantially homogenous in material properties, or in certain embodiments, can be heterogeneous, e.g., including a core and at least one shell. The optical properties of quantum dots can be influenced by their particle size, chemical composition, and/or surface composition, and can be determined by suitable optical testing available in the art. The ability to tailor the nanocrystal size, e.g., in the range between about 1 nm and about 15 nm, enables photoemission coverage in the entire optical spectrum to offer great versatility in color rendering.

A "ligand" is a molecule capable of interacting (whether weakly or strongly) with one or more facets of a nanostructure, e.g., through covalent, ionic, van der Waals, or other molecular interactions with the surface of the nanostructure.

"Photoluminescence quantum yield" is the ratio of photons emitted to photons absorbed, e.g., by a nanostructure or population of nanostructures. As known in the art, quantum yield is typically determined by a comparative method using well-characterized standard samples with known quantum yield values.

As used herein, the term "shell" refers to material deposited onto the core or onto previously deposited shells of the same or different composition and that result from a single act of deposition of the shell material. The exact shell thickness depends on the material as well as the precursor input and conversion and can be reported in nanometers or monolayers. As used herein, "target shell thickness" refers to the intended shell thickness used for calculation of the required precursor amount. As used herein, "actual shell thickness" refers to the actually deposited amount of shell material after the synthesis and can be measured by methods known in the art. By way of example, actual shell thickness can be measured by comparing particle diameters determined from transmission electron microscopy (TEM) images of nanocrystals before and after a shell synthesis.

As used herein, the term "solubilizing group" refers to a substantially non-polar group that has a low solubility in water and high solubility in organic solvents such as hexane, pentane, toluene, benzene, diethylether, acetone, ethyl acetate, dichloromethane (methylene chloride), chloroform, dimethylformamide, and N-methylpyrrolidinone. In some embodiments, the solubilizing group is a long-chain alkyl, a long-chain heteroalkyl, a long-chain alkenyl, a long-chain alkynyl, a cycloalkyl, or an aryl.

As used herein, the term "stable" refers to a mixture or composition that resists change or decomposition due to internal reaction or due to the action of air, heat, light, pressure, or other natural conditions.

As used herein, the term "full width at half-maximum" (FWHM) is a measure of the size distribution of quantum dots. The emission spectra of quantum dots generally have the shape of a Gaussian curve. The width of the Gaussian curve is defined as the FWHM and gives an idea of the size distribution of the particles. A smaller FWHM corresponds to a narrower quantum dot nanocrystal size distribution. FWHM is also dependent upon the emission wavelength maximum.

As used herein, the term "functional group equivalent weight" (FGEW) is used to determine the ratio of the reactive functional groups in a polymer. The FGEW of a polymer is defined as the ratio of the number average molecular weight (NAMW) to the number of functional groups in the polymer (n). It is the weight of a polymer that contains one formula weight of the functional group. The FGEW is calculated using end-group analysis by counting the number of reactive functional groups and dividing into the number average molecular weight:

$$FGEW=NAMW/n$$

where n=the number of reactive functional groups in the monomer.

As used herein, the term "polythiol" refers to simple or complex organic compounds containing at least two —SH groups per molecule.

As used herein, the term "alkane" refers to a saturated straight-chain, branched, or cyclic hydrocarbon having only single bonds. In some embodiments, the alkane includes from 1 to 20 carbon atoms. In some embodiments, the alkane is ethane, propane, butane, pentane, hexane, heptane, octane, nonane, or decane. Alkane groups can be substituted by one or more substituents, such as hydroxyl, halogen, amino, nitro, $C_{1-20}$ alkyl, or $C_{1-20}$ alkoxy.

As used herein, the term "alkene" refers to an unsaturated hydrocarbon that includes one or more carbon-carbon double bonds. In some embodiments, the alkene includes from 2 to 20 carbon atoms. In some embodiments, the alkene is ethene, propene, butene, pentene, hexene, heptene, octene, nonene, or decene. Alkene groups can be substituted by one or more substituents, such as hydroxyl, halogen, amino, nitro, $C_{1-20}$ alkyl, or $C_{1-20}$ alkoxy.

As used herein, the term "alkyl" refers to a straight or branched, saturated, aliphatic radical having the number of carbon atoms indicated. In some embodiments, the alkyl is $C_{1-2}$ alkyl, $C_{1-3}$ alkyl, $C_{1-4}$ alkyl, $C_{1-5}$ alkyl, $C_{1-6}$ alkyl, $C_{1-7}$ alkyl, $C_{1-8}$ alkyl, $C_{1-9}$ alkyl, $C_{1-10}$ alkyl, $C_{1-12}$ alkyl, $C_{1-14}$ alkyl, $C_{1-16}$ alkyl, $C_{1-18}$ alkyl, $C_{1-20}$ alkyl, $C_{8-20}$ alkyl, $C_{12-20}$ alkyl, $C_{14-20}$ alkyl, $C_{16-20}$ alkyl, or $C_{18-20}$ alkyl. For example, $C_{1-6}$ alkyl includes, but is not limited to, methyl, ethyl, propyl, isopropyl, butyl, isobutyl, sec-butyl, tert-butyl, pentyl, isopentyl, and hexyl. In some embodiments, the alkyl is octyl, nonyl, decyl, undecyl, dodecyl, tridecyl, tetradecyl, pentadecyl, hexadecyl, heptadecyl, octadecyl, nonadecyl, or icosanyl. Unless otherwise specified, the term "alkyl" may include "alkylene" groups.

As used herein, the term "heteroalkyl" refers to an alkyl moiety which is optionally substituted with one or more functional groups, and that contain one or more oxygen, sulfur, nitrogen, phosphorus, or silicon atoms, e.g., in place of carbon atoms.

As used herein, the term "cycloalkyl" refers to a monovalent or divalent group of 3 to 8 carbon atoms, preferably 3 to 5 carbon atoms derived from a saturated cyclic hydrocarbon. Cycloalkyl groups can be monocyclic or polycyclic. Cycloalkyl can be substituted by $C_{1-3}$ alkyl groups or halogens.

As used herein, the term "alkylene," refers to a saturated aliphatic group derived from a straight or branched chain saturated hydrocarbon attached at two or more positions having from 1 to about 20 carbon atoms. In some embodiments, the alkylene is $C_{1-2}$ alkylene, $C_{1-3}$ alkylene, $C_{1-4}$ alkylene, $C_{1-5}$ alkylene, $C_{1-6}$ alkylene, $C_{1-7}$ alkylene, $C_{1-8}$ alkylene, $C_{1-9}$ alkylene, $C_{1-10}$ alkylene, $C_{1-12}$ alkylene, $C_{1-14}$ alkylene, $C_{1-16}$ alkylene, $C_{1-18}$ alkylene, $C_{1-20}$ alkylene, $C_{8-20}$ alkylene, $C_{12-20}$ alkylene, $C_{14-20}$ alkylene, $C_{16-20}$ alkylene, or $C_{18-20}$ alkylene. For example, $C_{1-6}$ alkylene includes, but is not limited to, methylene, ethylene, propylene, isopropylene, butylene, isobutylene, sec-butylene, tert-butylene, pentylene, isopentylene, and hexylene. In some embodiments, the alkyl is octylene, nonylene, decylene, undecylene, dodecylene, tridecylene, tetradecylene, pentadecylene, hexadecylene, heptadecylene, octadecylene, nonadecylene, or icosanylene. Alkylene groups can be substituted by one or more substituents, such as hydroxyl, halogen, amino, nitro, $C_{1-20}$ alkyl, or $C_{1-20}$ alkoxy.

As used herein, the term "heteroalkylene" refers an alkylene group wherein one or more carbon atoms in its backbone are replaced by heteroatoms, such as oxygen, nitrogen, phosphorus, silicon, and sulfur, which includes, e.g., an oligomeric ethylene glycol moiety. Heteroalkylene groups can be substituted by one or more substituents, such as hydroxyl, halogen, amino, nitro, $C_{1-20}$ alkyl, or $C_{1-20}$ alkoxy.

As used herein, the term "amino" refers to $-NH_2$.

As used herein, the term "alkylamino" refers to a "substituted amino" of the formula ($-NR^K_2$), wherein $R^K$ is, independently, a hydrogen or an optionally substituted alkyl group, as defined herein, and the nitrogen moiety is directly attached to the parent molecule.

As used herein, the term "halo" or "halogen" refers to F, Cl, Br, or I.

As used herein, the term "alkoxy" refers to a straight or branched —O-alkyl group of 1 to 20 carbon atoms. In some embodiments, the alkoxy is $C_{1-2}$ alkoxy, $C_{1-3}$ alkoxy, $C_{1-4}$ alkoxy, $C_{1-5}$ alkoxy, $C_{1-6}$ alkoxy, $C_{1-7}$ alkoxy, $C_{1-8}$ alkoxy, $C_{1-9}$ alkoxy, $C_{1-10}$ alkoxy, $C_{1-12}$ alkoxy, $C_{1-14}$ alkoxy, $C_{1-16}$ alkoxy, $C_{1-18}$ alkoxy, $C_{1-20}$ alkoxy, $C_{8-20}$ alkoxy, $C_{12-20}$ alkoxy, $C_{14-20}$ alkoxy, $C_{16-20}$ alkoxy, or $C_{18-20}$ alkoxy. In some embodiments, the alkoxy is methoxy, ethoxy, n-propoxy, isopropoxy, or t-butoxy.

As used herein, the term "acrylate" or "acrylate group" refers to a compound bearing at least one moiety having the structure $-O-C(=O)-CH=CH_2$. In some embodiments, the acrylate is a methacrylate.

As used herein, the term "methacrylate" or "methacrylate group" refers to a compound bearing at least one moiety having the structure $-O-C(=O)-C(CH_3)=CH_2$.

As used herein, the term "acrylamide" or "acrylamide group" refers to a compound bearing at least one moiety having the structure $-NH-C(=O)-CH=CH_2$. In some embodiments, the acrylamide is a methacrylamide.

As used herein, the term "methacrylamide" or "methacrylamide group" refers to a compound bearing at least one moiety having the structure $-NH-C(=O)-C(CH_3)=CH_2$.

As used herein, the term "glycidyl ether" or "glycidyl ether group" refers to a compound bearing at least one moiety having the structure

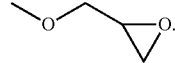

As used herein, the term "isocyanate" or "isocyanate group" refers to a compound bearing at least one moiety having the structure $-N=C=O$.

Unless clearly indicated otherwise, ranges listed herein are inclusive.

A variety of additional terms are defined or otherwise characterized herein.

Nanostructure Composition

In some embodiments, the present invention provides a nanostructure composition comprising:
(a) a nanostructure; and
(b) polythiol ligands bound to the surface of the nanostructure, wherein the polythiol ligands comprise a poly(ethylene oxide)/poly(propylene oxide) block copolymer, a poly(ethylene oxide) block copolymer, or a poly(propylene oxide) block copolymer.

In some embodiments, the present invention provides a nanostructure composition comprising:
(a) a nanostructure; and
(b) polythiol ligands dispersed on the surface of the nanostructure, the polythiol ligands having the formula I:

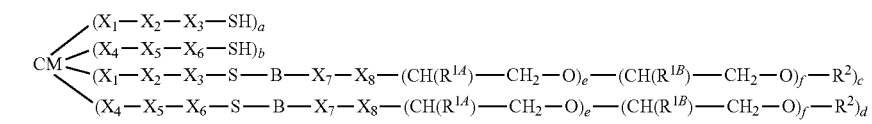

wherein:
CM is a central moiety;
$X_1$ is a bond, $-C(=O)-$, a $C_{1-10}$ alkylene, or a $C_{2-10}$ heteroalkylene;
$X_2$ is a bond, $-C(=O)-$, a $C_{1-10}$ alkylene, or a $C_{2-10}$ heteroalkylene;
$X_3$ is a bond, $-C(=O)-$, a $C_{1-10}$ alkylene, or a $C_{2-10}$ heteroalkylene;
$X_4$ is a bond, $-C(=O)-$, a $C_{1-10}$ alkylene, or a $C_{2-10}$ heteroalkylene;

$X_5$ is a bond, —C(=O)—, a $C_{1-10}$ alkylene, or a $C_{2-10}$ heteroalkylene;
$X_6$ is a bond, —C(=O)—, a $C_{1-10}$ alkylene, or a $C_{2-10}$ heteroalkylene;
B is —CH$_2$—CH$_2$—C(=O)—O—, —CH$_2$—C(CH$_3$)$_2$—C(=O)—O—, —CH$_2$—CH(CH$_3$)—C(=O)—NH—, —C(=O)—NH—, —CH$_2$—CH$_2$—, or —CH$_2$—CH(OH)—CH$_2$—O—;
$X_7$ is a bond or $C_{1-12}$ alkylene;
$X_8$ is a bond, —O—, —C(=O)—O—, or —C(=O)—N—;
$R^{1A}$ and $R^{1B}$ independently are H or $C_{1-20}$ alkyl;
$R^2$ is $C_{1-20}$ alkyl or $C_{1-20}$ alkoxy
a is 2 to 10;
b is 0 to 10;
c is 2 to 10;
d is 0 to 10;
e is 1 to 100; and
f is 0 to 100;
wherein a+b+c+d comprises a value within a range of 4 to 40.

In some embodiments, the present invention provides a nanostructure composition comprising:
(a) a nanostructure; and
(b) polythiol ligands dispersed on the surface of the nanostructure, the polythiol ligands having the formula II:

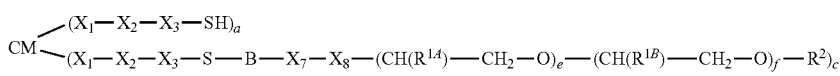

(II)

wherein:
CM is a central moiety;
$X_1$ is a bond, —C(=O)—, a $C_{1-10}$ alkylene, or a $C_{2-10}$ heteroalkylene;
$X_2$ is a bond, —C(=O)—, a $C_{1-10}$ alkylene, or a $C_{2-10}$ heteroalkylene;
$X_3$ is a bond, —C(=O)—, a $C_{1-10}$ alkylene, or a $C_{2-10}$ heteroalkylene;
B is —CH$_2$—CH$_2$—C(=O)—O—, —CH$_2$—C(CH$_3$)$_2$—C(=O)—O—, —CH$_2$—CH(CH$_3$)—C(=O)—NH—, —C(=O)—NH—, —CH$_2$—CH$_2$—, or —CH$_2$—CH(OH)—CH$_2$—O—;
$X_7$ is a bond or $C_{1-12}$ alkylene;
$X_8$ is a bond, —O—, —C(=O)—O—, or —C(=O)—N—;
$R^{1A}$ and $R^{1B}$ independently are H or $C_{1-20}$ alkylene;
$R^2$ is $C_{1-20}$ alkylene or $C_{1-20}$ alkoxy;
a is 2 to 10;
c is 2 to 10;
e is 1 to 100; and
f is 0 to 100;
wherein a +c≥4 and ≤20.

In some embodiments, the present invention provides a nanostructure composition comprising:
(a) at least one population of nanostructures, wherein between about 20 and about 100 mole percent of ligands in at least one population of nanostructures comprise a polythiol ligand bound to the nanostructures; and
(b) at least one organic resin.
In some embodiments, the nanostructure composition further comprises a solvent.

In some embodiments, the nanostructure composition further comprises a polar organic solvent.
In some embodiments, the nanostructure is a quantum dot.
In some embodiments, the present invention provides a nanostructure film kit comprising:
(a) a first composition comprising at least one population of nanostructures, wherein between about 20 and about 100 mole percent of ligands in at least one population of nanostructures comprise a polythiol ligand bound to the nanostructures;
(b) a second composition comprising at least one organic resin; and
(c) instructions for preparing a nanostructure film.
In some embodiments, the nanostructure film kit further comprises a solvent. In some embodiments, the nanostructure film kit further comprises a polar organic solvent.
In some embodiments, the nanostructure is a quantum dot.

Nanostructure Film Layer

In some embodiments, the present invention provides a nanostructure film layer comprising:
(a) at least one population of nanostructures, wherein between about 20 and about 100 mole percent of ligands in at least one population of nanostructures comprises a polythiol ligand bound to the nanostructures; and
(b) at least one organic resin.
In some embodiments, the nanostructure is a quantum dot.

Nanostructure Molded Article

In some embodiments, the present invention provides a nanostructure molded article comprising:
(a) at least one population of nanostructures, wherein between about 20 and about 100 mole percent of ligands in at least one population of nanostructures comprise a polythiol ligand bound to the nanostructures; and
(b) at least one organic resin.
In some embodiments, the molded article is a film, a substrate for a display, or a light emitting diode.
In some embodiments, the nanostructure is a quantum dot.
In some embodiments, the present invention provides a nanostructure film comprising:
(a) a first barrier layer;
(b) a second barrier layer; and
(c) a nanostructure layer between the first barrier layer and the second barrier layer, wherein the nanostructure layer comprises at least one population of nanostructures, wherein between about 20 and about 100 mole percent of ligands in at least one population of nanostructures comprise a polythiol ligand bound to the nanostructures; and at least one organic resin.
In some embodiments, the nanostructure is a quantum dot.

Nanostructures

In some embodiments, the nanostructure comprises a core and at least one shell. In some embodiments, the nanostructure comprises a core and 1, 2, 3, 4, 5, 6, 7, 8, 9, or 10 shells. In some embodiments, the nanostructure comprises a core and one shell. In some embodiments, the nanostructure comprises a core and two shells. In some embodiments, the nanostructure comprises a core and three shells. In some embodiments, the nanostructure comprises at least two shells wherein the two shells are different.

The number of monolayers will determine the size of the core/shell(s) nanostructures. The size of the core/shell(s) nanostructures can be determined using techniques known to those of skill in the art. In some embodiments, the size of the core/shell(s) nanostructures is determined using TEM. In some embodiments, the core/shell(s) nanostructures have an average diameter of between about 1 nm and about 15 nm, about 1 nm and about 10 nm, about 1 nm and about 9 nm, about 1 nm and about 8 nm, about 1 nm and about 7 nm, about 1 nm and about 6 nm, about 1 nm and about 5 nm, about 5 nm and about 15 nm, about 5 nm and about 10 nm, about 5 nm and about 9 nm, about 5 nm and about 8 nm, about 5 nm and about 7 nm, about 5 nm and about 6 nm, about 6 nm and about 15 nm, about 6 nm and about 10 nm, about 6 nm and about 9 nm, about 6 nm and about 8 nm, about 6 nm and about 7 nm, about 7 nm and about 15 nm, about 7 nm and about 10 nm, about 7 nm and about 9 nm, about 7 nm and about 8 nm, about 8 nm and about 15 nm, about 8 nm and about 10 nm, about 8 nm and about 9 nm, about 9 nm and about 15 nm, about 9 nm and about 10 nm, or about 10 nm and about 15 nm. In some embodiments, the core/shell(s) nanostructures have an average diameter of between about 6 nm and about 7 nm.

Nanostructure Cores

In some embodiments, the core comprises Si, Ge, Sn, Se, Te, B, C, P, BN, BP, BAs, AlN, AlP, AlAs, AlSb, GaN, GaP, GaAs, GaSb, InN, InP, InAs, InSb, ZnO, ZnS, ZnSe, ZnTe, CdS, CdSe, CdSeZn, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCi, CuBr, CuI, $Si_3N_4$, $Ge_3N_4$, $Al_2O_3$, $Al_2OC$, or combinations thereof.

In some embodiments, the core is a Group III-V nanostructure. In some embodiments, the core is a Group III-V nanocrystal selected from the group consisting of BN, BP, BAs, BSb, AlN, AlP, AlAs, AlSb, GaN, GaP, GaAs, GaSb, InN, InP, InAs, and InSb. In some embodiments, the core is an InP nanocrystal.

The synthesis of Group III-V nanostructures has been described in U.S. Pat. Nos. 5,505,928, 6,306,736, 6,576,291, 6,788,453, 6,821,337, 7,138,098, 7,557,028, 8,062,967, 7,645,397, and 8,282,412 and in U.S. Patent Appl. Publication No. 2015/236195. Synthesis of Group III-V nanostructures has also been described in Wells, R. L., et al., "The use of tris(trimethylsilyl)arsine to prepare gallium arsenide and indium arsenide," *Chem. Mater.* 1:4-6 (1989) and in Guzelian, A. A., et al., "Colloidal chemical synthesis and characterization of InAs nanocrystal quantum dots," *Appl. Phys. Lett.* 69: 1432-1434 (1996).

Synthesis of InP-based nanostructures has been described, e.g., in Xie, R., et al., "Colloidal InP nanocrystals as efficient emitters covering blue to near-infrared," *J. Am. Chem. Soc.* 129:15432-15433 (2007); Micic, O. I., et al., "Core-shell quantum dots of lattice-matched $ZnCdSe_2$ shells on InP cores: Experiment and theory," *J. Phys. Chem. B* 104:12149-12156 (2000); Liu, Z., et al., "Coreduction colloidal synthesis of III-V nanocrystals: The case of InP," *Angew. Chem. Int. Ed. Engl.* 47:3540-3542 (2008); Li, L. et al., "Economic synthesis of high quality InP nanocrystals using calcium phosphide as the phosphorus precursor," *Chem. Mater.* 20:2621-2623 (2008); D. Battaglia and X. Peng, "Formation of high quality InP and InAs nanocrystals in a noncoordinating solvent," *Nano Letters* 2:1027-1030 (2002); Kim, S., et al., "Highly luminescent InP/GaP/ZnS nanocrystals and their application to white light-emitting diodes," *J. Am. Chem. Soc.* 134:3804-3809 (2012); Nann, T., et al., "Water splitting by visible light: A nanophotocathode for hydrogen production," *Angew. Chem. Int. Ed.* 49:1574-1577 (2010); Borchert, H., et al., "Investigation of ZnS passivated InP nanocrystals by XPS," *Nano Letters* 2:151-154 (2002); L. Li and P. Reiss, "One-pot synthesis of highly luminescent InP/ZnS nanocrystals without precursor injection," *J. Am. Chem. Soc.* 130:11588-11589 (2008); Hussain, S., et al. "One-pot fabrication of high-quality InP/ZnS (core/shell) quantum dots and their application to cellular imaging," *Chemphyschem.* 10:1466-1470 (2009); Xu, S., et al., "Rapid synthesis of high-quality InP nanocrystals," *J. Am. Chem. Soc.* 128:1054-1055 (2006); Micic, O. I., et al., "Size-dependent spectroscopy of InP quantum dots," *J. Phys. Chem. B* 101:4904-4912 (1997); Haubold, S., et al., "Strongly luminescent InP/ZnS core-shell nanoparticles," *Chemphyschem.* 5:331-334 (2001); CrosGagneux, A., et al., "Surface chemistry of InP quantum dots: A comprehensive study," *J. Am. Chem. Soc.* 132:18147-18157 (2010); Micic, O. I., et al., "Synthesis and characterization of InP, GaP, and $GaInP_2$ quantum dots," *J. Phys. Chem.* 99:7754-7759 (1995); Guzelian, A. A., et al., "Synthesis of size-selected, surface-passivated InP nanocrystals," *J. Phys. Chem.* 100: 7212-7219 (1996); Lucey, D. W., et al., "Monodispersed InP quantum dots prepared by colloidal chemistry in a non-coordinating solvent," *Chem. Mater.* 17:3754-3762 (2005); Lim, J., et al., "InP@ZnSeS, core@composition gradient shell quantum dots with enhanced stability," *Chem. Mater.* 23:4459-4463 (2011); and Zan, F., et al., "Experimental studies on blinking behavior of single InP/ZnS quantum dots: Effects of synthetic conditions and UV irradiation," *J. Phys. Chem. C* 116:394-3950 (2012). However, such efforts have had only limited success in producing InP nanostructures with high quantum yields.

In some embodiments, the core is doped. In some embodiments, the dopant of the nanocrystal core comprises a metal, including one or more transition metals. In some embodiments, the dopant is a transition metal selected from the group consisting of Ti, Zr, Hf, V, Nb, Ta, Cr, Mo, W, Mn, Tc, Re, Fe, Ru, Os, Co, Rh, Ir, Ni, Pd, Pt, Cu, Ag, Au, and combinations thereof. In some embodiments, the dopant comprises a non-metal. In some embodiments, the dopant is ZnS, ZnSe, ZnTe, CdSe, CdS, CdTe, HgS, HgSe, HgTe, $CuInS_2$, $CuInSe_2$, AlN, AlP, AlAs, GaN, GaP, or GaAs.

In some embodiments, the core is a Group II-VI nanocrystal selected from the group consisting of ZnO, ZnSe, ZnS, ZnTe, CdO, CdSe, CdS, CdTe, HgO, HgSe, HgS, and HgTe. In some embodiments, the core is a nanocrystal selected from the group consisting of ZnSe, ZnS, CdSe, and CdS. The synthesis of Group II-VI nanostructures has been described in U.S. Pat. Nos. 6,225,198, 6,322,901, 6,207,229, 6,607,829, 7,060,243, 7,374,824, 6,861,155, 7,125,605, 7,566,476, 8,158,193, and 8,101,234 and in U.S. Patent Appl. Publication Nos. 2011/0262752 and 2011/0263062.

In some embodiments, the core is purified before deposition of a shell. In some embodiments, the core is filtered to remove precipitate from the core solution.

In some embodiments, the core is subjected to an acid etching step before deposition of a shell.

In some embodiments, the diameter of the core is determined using quantum confinement. Quantum confinement in zero-dimensional nanocrystallites, such as quantum dots, arises from the spatial confinement of electrons within the crystallite boundary. Quantum confinement can be observed once the diameter of the material is of the same magnitude as the de Broglie wavelength of the wave function. The electronic and optical properties of nanoparticles deviate substantially from those of bulk materials. A particle behaves as if it were free when the confining dimension is large compared to the wavelength of the particle. During this state, the band gap remains at its original energy due to a continuous energy state. However, as the confining dimension decreases and reaches a certain limit, typically in nanoscale, the energy spectrum becomes discrete. As a result, the band gap becomes size-dependent. Size can be determined as is known in the art, for example, using transmission electron microscopy and/or physical modeling.

In some embodiments, the diameter of the core nanostructure is between about 1 nm and about 9 nm, about 1 nm and about 8 nm, about 1 nm and about 7 nm, about 1 nm and about 6 nm, about 1 nm and about 5 nm, about 1 nm and about 4 nm, about 1 nm and about 3 nm, about 1 nm and about 2 nm, about 2 nm and about 9 nm, about 2 nm and about 8 nm, about 2 nm and about 7 nm, about 2 nm and about 6 nm, about 2 nm and about 5 nm, about 2 nm and about 4 nm, about 2 nm and about 3 nm, about 3 nm and about 9 nm, about 3 nm and about 8 nm, about 3 nm and about 7 nm, about 3 nm and about 6 nm, about 3 nm and about 5 nm, about 3 nm and about 4 nm, about 4 nm and about 9 nm, about 4 nm and about 8 nm, about 4 nm and about 7 nm, about 4 nm and about 6 nm, about 4 nm and about 5 nm, about 5 nm and about 9 nm, about 5 nm and about 8 nm, about 5 nm and about 7 nm, about 5 nm and about 6 nm, about 6 nm and about 9 nm, about 6 nm and about 8 nm, about 6 nm and about 7 nm, about 7 nm and about 9 nm, about 7 nm and about 8 nm, or about 8 nm and about 9 nm. In some embodiments, the diameter of the core nanostructures is about 7 nm.

Nanostructure Shell Layers

The shell can, e.g., increase the quantum yield and/or stability of the nanostructures. In some embodiments, the core and the shell comprise different materials. In some embodiments, the nanostructure comprises shells of different shell material.

In some embodiments, a shell that comprises a mixture of Group II and VI elements is deposited onto a core or a core/shell(s) structure. In some embodiments, the shell is deposited by a mixture of at least two of a zinc source, a selenium source, a sulfur source, a tellurium source, and a cadmium source. In some embodiments, the shell is deposited by a mixture of two of a zinc source, a selenium source, a sulfur source, a tellurium source, and a cadmium source. In some embodiments, the shell is deposited by a mixture of three of a zinc source, a selenium source, a sulfur source, a tellurium source, and a cadmium source. In some embodiments, the shell is composed of zinc and sulfur; zinc and selenium; zinc, sulfur, and selenium; zinc and tellurium; zinc, tellurium, and sulfur; zinc, tellurium, and selenium; zinc, cadmium, and sulfur; zinc, cadmium, and selenium; cadmium and sulfur; cadmium and selenium; cadmium, selenium, and sulfur; cadmium, zinc, and sulfur; cadmium, zinc, and selenium; or cadmium, zinc, sulfur, and selenium.

In some embodiments, the at least one shell comprises CdS, CdSe, CdO, CdTe, ZnS, ZnO, ZnSe, ZnTe, MgTe, GaAs, GaSb, GaN, HgO, HgS, HgSe, HgTe, InAs, InSb, InN, AlAs, AlN, AlSb, AlS, PbS, PbO, PbSe, PbTe, MgO, MgS, MgSe, MgTe, CuCl, Ge, Si, or alloys thereof. In some embodiments, the at least one shell comprises ZnSe. In some embodiments, the at least one shell comprises ZnS. In some embodiments, the at least one shell comprises a first shell comprising ZnSe and a second shell comprising ZnS.

In some embodiments, a shell comprises more than one monolayer of shell material. The number of monolayers is an average for all the nanostructures; therefore, the number of monolayers in a shell can be a fraction. In some embodiments, the number of monolayers in a shell is between 0.25 and 10, 0.25 and 8, 0.25 and 7, 0.25 and 6, 0.25 and 5, 0.25 and 4, 0.25 and 3, 0.25 and 2, 2 and 10, 2 and 8, 2 and 7, 2 and 6, 2 and 5, 2 and 4, 2 and 3, 3 and 10, 3 and 8, 3 and 7, 3 and 6, 3 and 5, 3 and 4, 4 and 10, 4 and 8, 4 and 7, 4 and 6, 4 and 5, 5 and 10, 5 and 8, 5 and 7, 5 and 6, 6 and 10, 6 and 8, 6 and 7, 7 and 10, 7 and 8, or 8 and 10. In some embodiments, the shell comprises between 3 and 5 monolayers.

The thickness of each shell can be determined using techniques known to those of skill in the art. In some embodiments, the thickness of each shell is determined by comparing the average diameter of the nanostructure before and after the addition of each shell. In some embodiments, the average diameter of the nanostructure before and after the addition of each shell is determined by TEM.

In some embodiments, each shell has a thickness of between about 0.05 nm and about 3.5 nm, about 0.05 nm and about 2 nm, about 0.05 nm and about 0.9 nm, about 0.05 nm and about 0.7 nm, about 0.05 nm and about 0.5 nm, about 0.05 nm and about 0.3 nm, about 0.05 nm and about 0.1 nm, about 0.1 nm and about 3.5 nm, about 0.1 nm and about 2 nm, about 0.1 nm and about 0.9 nm, about 0.1 nm and about 0.7 nm, about 0.1 nm and about 0.5 nm, about 0.1 nm and about 0.3 nm, about 0.3 nm and about 3.5 nm, about 0.3 nm and about 2 nm, about 0.3 nm and about 0.9 nm, about 0.3 nm and about 0.7 nm, about 0.3 nm and about 0.5 nm, about 0.5 nm and about 3.5 nm, about 0.5 nm and about 2 nm, about 0.5 nm and about 0.9 nm, about 0.5 nm and about 0.7 nm, about 0.7 nm and about 3.5 nm, about 0.7 nm and about 2 nm, about 0.7 nm and about 0.9 nm, about 0.9 nm and about 3.5 nm, about 0.9 nm and about 2 nm, or about 2 nm and about 3.5 nm.

Ligand Exchange

The present disclosure is directed to a method of replacing a first ligand on a nanostructure with a second ligand. In some embodiments, the second ligand is a polythiol ligand. In some embodiments, the nanostructure is a quantum dot.

In some embodiments, the present disclosure is directed to a method of replacing a first ligand on a nanostructure with a second ligand comprising admixing a reaction mixture comprising a population of nanostructures having a first ligand bound to the nanostructure and at least one second ligand, such that the second ligand displaces the first ligand and becomes bound to the nanostructure.

In some embodiments, the nanostructure is a quantum dot.

In some embodiments, the admixing is performed at a temperature between about 0° C. and about 200° C., about 0° C. and about 150° C., about 0° C. and about 100° C., about 0° C. and about 80° C., about 20° C. and about 200° C., about 20° C. and about 150° C., about 20° C. and about 100° C., about 20° C. and about 80° C., about 50° C. and about 200° C., about 50° C. and about 150° C., about 50° C. and about 100° C., about 50° C. and about 80° C., about 80° C. and about 200° C., about 80° C. and about 150° C., about 80° C. and about 100° C., about 100° C. and about 200° C., about 100° C. and about 150° C., or about 150° C. and about 200° C. In some embodiments, the admixing is performed at a temperature between about 20° C. and about 100° C. In some embodiments, the admixing is performed at a temperature of about 22° C. In some embodiments, the admixing is performed at a temperature of about 70° C.

In some embodiments, the admixing is performed over a period of between about 1 minute and about 6 hours, about 1 minute and about 2 hours, about 1 minute and about 1 hour, about 1 minute and about 40 minutes, about 1 minute and about 30 minutes, about 1 minute and about 20 minutes, about 1 minute and about 10 minutes, about 10 minutes and about 6 hours, about 10 minutes and about 2 hours, about 10 minutes and about 1 hour, about 10 minutes and about 40 minutes, about 10 minutes and about 30 minutes, about 10 minutes and about 20 minutes, about 20 minutes and about 6 hours, about 20 minutes and about 2 hours, about 20 minutes and about 1 hour, about 20 minutes and about 40 minutes, about 20 minutes and about 30 minutes, about 30 minutes and about 6 hours, about 30 minutes and about 2 hours, about 30 minutes and about 1 hour, about 30 minutes and about 40 minutes, about 40 minutes and about 6 hours, about 40 minutes and about 2 hours, about 40 minutes and about 1 hour, about 1 hour and about 6 hours, about 1 hour and about 2 hours, or about 2 hours and about 6 hours.

In some embodiments, the reaction mixture further comprises a solvent. In some embodiments, the solvent is selected from the group consisting of chloroform, acetone, butanone, tetrahydrofuran, 2-methyltetrahydrofuran, ethylene glycol monoethyl ether, ethylene glycol monopropyl ether, ethylene glycol monobutyl ether, diethylene glycol diethyl ether, methyl isobutyl ketone, monomethyl ether glycol ester, gamma-butyrolactone, methylacetic-3-ethyl ether, butyl carbitol, butyl carbitol acetate, propanediol monomethyl ether, propanediol monomethyl ether acetate, cyclohexane, toluene, xylene, isopropyl alcohol, N-methylformamide, and combinations thereof. In some embodiments, the solvent is toluene. In some embodiments, the solvent is N-methylformamide. In some embodiments, the solvent is a mixture of toluene and N-methylformamide.

The percentage of second ligands that are bound to a nanostructure in a population of nanostructures can be measured by $^1$H NMR, wherein the bound ligands are calculated using: (bound second ligands)/(bound+free second ligands).

In some embodiments, the mole percentage of second ligands bound to a population of nanostructures is between about 20% and about 100%, about 20% and about 80%, about 20% and about 60%, about 20% and about 40%, about 25% and about 100%, about 25% and about 80%, about 25% and about 60%, about 25% and about 40%, about 30% and about 100%, about 30% and about 80%, about 30% and about 60%, about 30% and about 40%, about 40% and about 100%, about 40% and about 80%, about 40% and about 60%, about 60% and about 100%, about 60% and about 80%, or about 80% and about 100%.

disclosed in U.S. Pat. Nos. 7,572,395, 8,143,703, 8,425,803, 8,563,133, 8,916,064, 9,005,480, 9,139,770, and 9,169,435, and in U.S. Patent Application Publication No. 2008/0118755.

In some embodiments, the first ligand is a fatty acid selected from the group consisting of lauric acid, caproic acid, myristic acid, palmitic acid, stearic acid, and oleic acid. In some embodiments, the first ligand is an organic phosphine or an organic phosphine oxide selected from trioctylphosphine oxide, trioctylphosphine, diphenylphosphine, triphenylphosphine oxide, and tributylphosphine oxide. In some embodiments, the first ligand is an amine selected from the group consisting of dodecylamine, oleylamine, hexadecylamine, dioctylamine, and octadecylamine. In some embodiments, the first ligand is trioctylphosphine, trioctylphosphine oxide, trihydroxypropyl phosphine, tributylphosphine, tridodecylphosphine, dibutyl phosphite, tributyl phosphite, octadecyl phosphite, trilauryl phosphite, didodecyl phosphite, triisodocyl phosphite, bis (2-ethylhexyl) phosphate, tridecyl phosphate, hexadecylamine, oleylamine, octadecylamine, dioctadecylamine, octacosamine, bis (2-ethylhexyl) amine, octylamine, dioctylamine, trioctylamine, dodecylamine, didodecylamine, hexadecylamine, phenyl phosphoric acid, hexylphosphoric acid, tetradecylphosphonic acid, octyl phosphoric acid, n-octadecylphosphonic acid, propenyldiphosphonic acid, dioctyl ether, diphenyl ether, octyl mercaptan, dodecyl mercaptan, oleate, or octanethiol. In some embodiments, the first ligand is oleate, trioctylphosphine, or octanethiol.

Second Ligands

In some embodiments, the second ligand is polythiol ligand comprising at least one —SH group. In some embodiments, the at least one —SH group can bind to II-VI nanocrystal surfaces as a neutral L-type binding ligand (e.g., R—COOH). In some embodiments, the at least one —SH group can bind to II-VI nanocrystal surfaces as an electron donating X-type ligand (e.g., R—COO$^-$).

In some embodiments, the polythiol ligand is prepared by reacting a polythiol with a poly(alkylene oxide) compound comprising an acrylate group, a methacrylate group, an acrylamide group, an isocyanate group, an alkene group, or a glycidyl ether group to produce a polythiol ligand.

Polythiol

In some embodiments, the polythiol has formula III:

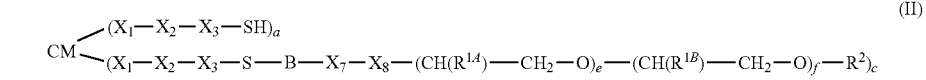

(II)

First Ligands

In some embodiments, each shell is synthesized in the presence of at least one nanostructure ligand. Ligands can, e.g., enhance the miscibility of nanostructures in solvents or polymers (allowing the nanostructures to be distributed throughout a composition such that the nanostructures do not aggregate together), increase quantum yield of nanostructures, and/or preserve nanostructure luminescence (e.g., when the nanostructures are incorporated into a matrix). In some embodiments, the ligand(s) for the core synthesis and for the shell synthesis are the same. In some embodiments, the ligand(s) for the core synthesis and for the shell synthesis are different. Following synthesis, any ligand on the surface of the nanostructures can be exchanged for a different ligand with other desirable properties. Examples of ligands are wherein:
  CM is a central moiety;
  $X_1$ is a bond, —C(=O), a $C_{1-10}$ alkylene, or a $C_{2-10}$ heteroalkylene;
  $X_2$ is a bond, —C(=O), a $C_{1-10}$ alkylene, or a $C_{2-10}$ heteroalkylene;
  $X_3$ is a bond, —C(=O), a $C_{1-10}$ alkylene, or a $C_{2-10}$ heteroalkylene;
  $X_4$ is a bond, —C(=O), a $C_{1-10}$ alkylene, or a $C_{2-10}$ heteroalkylene;
  $X_5$ is a bond, —C(=O), a $C_{1-10}$ alkylene, or a $C_{2-10}$ heteroalkylene;
  $X_6$ is a bond, —C(=O), a $C_{1-10}$ alkylene, or a $C_{2-10}$ heteroalkylene;

a is 2 to 10; and b is 0 to 10;

and wherein a+b≥3 and ≤20.

In some embodiments, where b is 0 in formula III, the polythiol has formula IV:

$$CM\text{-}(X_1\text{---}X_2\text{---}X_3\text{---}SH)_a \quad (IV)$$

wherein:

CM is a central moiety;

$X_1$ is a bond, —C(=O)—, a $C_{1-10}$ alkylene, or a $C_{2-10}$ heteroalkylene;

$X_2$ is a bond, —C(=O)—, a $C_{1-10}$ alkylene, or a $C_{2-10}$ heteroalkylene;

$X_3$ is a bond, —C(=O)—, a $C_{1-10}$ alkylene, or a $C_{2-10}$ heteroalkylene; and a is 3 to 10.

In some embodiments, CM is an alkane, 1,3,5-triazine, pentaerythritol, 1,3,5-triazine-2,4,6-trione, trimethylolpropane, or (propane-2,2-diylbis(4,1-phenylene))bis(λ'-oxy). In some embodiments, CM is propane.

In some embodiments, $X_1$ is a bond. In some embodiments, $X_1$ is —C(=O)—. In some embodiments, $X_1$ is a substituted or unsubstituted $C_{1-10}$ alkylene. In some embodiments, $X_1$ is an unsubstituted $C_{1-10}$ alkylene. In some embodiments, $X_1$ is a substituted $C_{1-10}$ alkylene. In some embodiments, $X_1$ is a substituted or unsubstituted $C_{1-10}$ heteroalkylene. In some embodiments, $X_1$ is an unsubstituted $C_{1-10}$ heteroalkylene. In some embodiments, $X_1$ is a substituted $C_{1-10}$ heteroalkylene. In some embodiments, the substituent on $X_1$ is a —SH.

In some embodiments, $X_2$ is a bond. In some embodiments, $X_2$ is —C(=O)—. In some embodiments, $X_2$ is a substituted or unsubstituted $C_{1-10}$ alkylene. In some embodiments, $X_2$ is an unsubstituted $C_{1-10}$ alkylene. In some embodiments, $X_2$ is a substituted $C_{1-10}$ alkylene. In some embodiments, $X_2$ is a substituted or unsubstituted $C_{1-10}$ heteroalkylene. In some embodiments, $X_2$ is an unsubstituted $C_{1-10}$ heteroalkylene. In some embodiments, $X_2$ is a substituted $C_{1-10}$ heteroalkylene. In some embodiments, the substituent on $X_2$ is a —SH.

In some embodiments, $X_3$ is a bond. In some embodiments, $X_3$ is —C(=O)—. In some embodiments, $X_3$ is a substituted or unsubstituted $C_{1-10}$ alkylene. In some embodiments, $X_3$ is an unsubstituted $C_{1-10}$ alkylene. In some embodiments, $X_3$ is a substituted $C_{1-10}$ alkylene. In some embodiments, $X_3$ is a substituted or unsubstituted $C_{1-10}$ heteroalkylene. In some embodiments, $X_3$ is an unsubstituted $C_{1-10}$ heteroalkylene. In some embodiments, $X_3$ is a substituted $C_{1-10}$ heteroalkylene. In some embodiments, the substituent on $X_3$ is a —SH.

In some embodiments, $X_4$ is a bond. In some embodiments, $X_4$ is —C(=O)—. In some embodiments, $X_4$ is a substituted or unsubstituted $C_{1-10}$ alkylene. In some embodiments, $X_4$ is an unsubstituted $C_{1-10}$ alkylene. In some embodiments, $X_4$ is a substituted $C_{1-10}$ alkylene. In some embodiments, $X_4$ is a substituted or unsubstituted $C_{1-10}$ heteroalkylene. In some embodiments, $X_4$ is an unsubstituted $C_{1-10}$ heteroalkylene. In some embodiments, $X_4$ is a substituted $C_{1-10}$ heteroalkylene. In some embodiments, the substituent on $X_4$ is a —SH.

In some embodiments, $X_5$ is a bond. In some embodiments, $X_5$ is —C(=O)—. In some embodiments, $X_5$ is a substituted or unsubstituted $C_{1-10}$ alkylene. In some embodiments, $X_5$ is an unsubstituted $C_{1-10}$ alkylene. In some embodiments, $X_5$ is a substituted $C_{1-10}$ alkylene. In some embodiments, $X_5$ is a substituted or unsubstituted $C_{1-10}$ heteroalkylene. In some embodiments, $X_5$ is an unsubstituted $C_{1-10}$ heteroalkylene. In some embodiments, $X_5$ is a substituted $C_{1-10}$ heteroalkylene. In some embodiments, the substituent on $X_5$ is a —SH.

In some embodiments, $X_6$ is a bond. In some embodiments, $X_6$ is —C(=O)—. In some embodiments, $X_6$ is a substituted or unsubstituted $C_{1-10}$ alkylene. In some embodiments, $X_6$ is an unsubstituted $C_{1-10}$ alkylene. In some embodiments, $X_6$ is a substituted $C_{1-10}$ alkylene. In some embodiments, $X_6$ is a substituted or unsubstituted $C_{1-10}$ heteroalkylene. In some embodiments, $X_6$ is an unsubstituted $C_{1-10}$ heteroalkylene. In some embodiments, $X_6$ is a substituted $C_{1-10}$ heteroalkylene. In some embodiments, the substituent on $X_6$ is a —SH.

In some embodiments, a is between 2 and 10. In some embodiments, a is between 3 and 10. In some embodiments, a is between 2 and 10, 2 and 8, 2 and 6, 2 and 4, 2 and 3, 3 and 10, 3 and 8, 3 and 6, 3 and 4, 4 and 10, 4 and 8, 4 and 6, 6 and 10, 6 and 8, or 8 and 10.

In some embodiments, b is between 0 and 10. In some embodiments, b is between 0 and 10, 0 and 8, 0 and 6, 0 and 4, 3 and 10, 3 and 8, 3 and 6, 6 and 10, 6 and 8, or 8 and 10. In some embodiments, b is 0.

In some embodiments, $X_1$, $X_2$, and $X_3$ are a bond and b is 0.

In some embodiments, $X_1$ is —C(=O)—, $X_2$ is unsubstituted $C_{1-10}$ alkylene, and b is 0.

In some embodiments, $X_1$ is —C(=O)—, $X_2$ is a branched unsubstituted $C_{1-10}$ alkylene, $X_3$ is a bond, and b is 0.

In some embodiments, $X_1$ is $C_{1-10}$ heteroalkylene, $X_2$ is —C(=O)—, $X_3$ is unsubstituted $C_{1-10}$ alkylene, and b is 0.

In some embodiments, $X_1$ is a substituted $C_{1-10}$ heteroalkylene, wherein the substituent is a —SH, and b is 0.

In some embodiments, $X_1$ is $C_{1-10}$ alkylene, $X_2$ is —C(=O)—, $X_3$ is unsubstituted $C_{1-10}$ alkylene, a is 2, and b is 1.

In some embodiments, the polythiol is a commercially available polythiol.

In some embodiments, the polythiol is selected from the group consisting of:

| Chemical Name | Chemical Structure |
|---|---|
| Propane-1,2,3-trithiol | 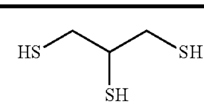 |

| Chemical Name | Chemical Structure |
|---|---|
| Trithiocyanuric acid | A 1,3,5-triazine ring with SH groups at the 2, 4, and 6 positions. |
| Pentaerythritol tetrakis(3-mercaptopropionate) | C(CH$_2$OC(O)CH$_2$CH$_2$SH)$_4$ |
| Trimethylolpropane tris(thioglycolate) | CH$_3$CH$_2$C(CH$_2$OC(O)CH$_2$SH)$_3$ |
| Trimethylolpronae tris(3-mercaptopropionate) | CH$_3$CH$_2$C(CH$_2$OC(O)CH$_2$CH$_2$SH)$_3$ |
| Pentaerythritol tetrakis(thioglycolate) | C(CH$_2$OC(O)CH$_2$SH)$_4$ |
| Pentaerythritol tetrakis(3-mercaptopropionate) | C(CH$_2$OC(O)CH$_2$CH$_2$SH)$_4$ |

| Chemical Name | Chemical Structure |
|---|---|
| Pentraerythritol tetrakis(3-mercaptobutylate) | 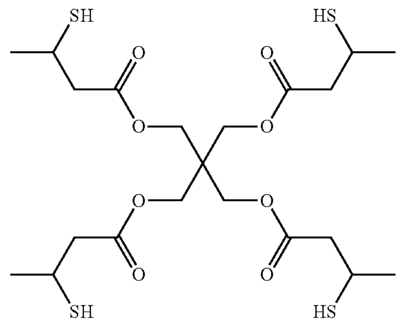 [SMILES: CC(S)CC(=O)OCC(COC(=O)CC(C)S)(COC(=O)CC(C)S)COC(=O)CC(C)S] |
| Tris[2-(3-mercaptopropionyloxy) ethyl]isocyanurate | 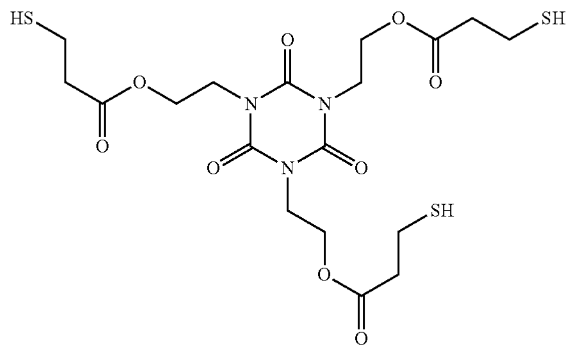 [SMILES: O=C(CCS)OCCn1c(=O)n(CCOC(=O)CCS)c(=O)n(CCOC(=O)CCS)c1=O] |
| 2-((3-(4-mercapto-2-oxobutoxy)-2-(((5-mercapto-2-oxopentyl)oxy)methyl)-2-(((3-mercaptopropanoyl)oxy)methyl)propoxy)methyl)-2-((4-mercapto-2-oxobutoxy)methyl)propane-1,3-diylbis(3-mercaptopropanoate) | 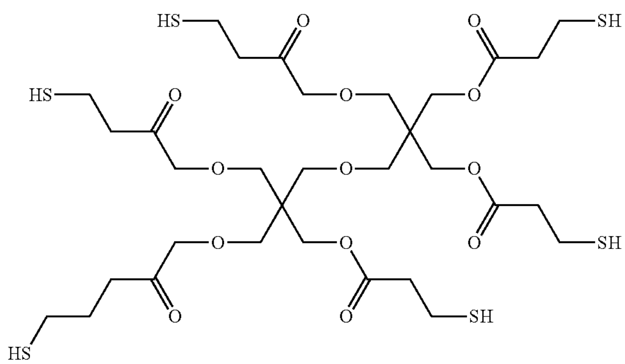 [SMILES: O=C(CCS)COCC(COCC(=O)CCCS)(COCC(COCC(=O)CCS)(COC(=O)CCS)COC(=O)CCS)COC(=O)CCS] |
| 2,2-bis(((3-mercaptobutanoyl)oxy)methyl)propane-1,3-diyl bis(3-mercapto-butanoate) | 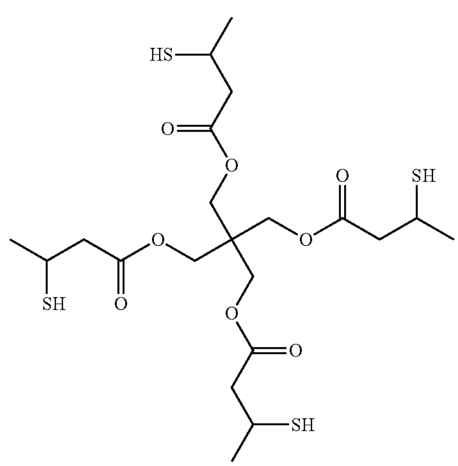 [SMILES: CC(S)CC(=O)OCC(COC(=O)CC(C)S)(COC(=O)CC(C)S)COC(=O)CC(C)S] |

| Chemical Name | Chemical Structure |
|---|---|
| 3,3'-((((propane-2,2-diylbis(4,1-phenylene))bis(oxy))bis(2-mercaptopropane-3,1-diyl))bis(sulfanediyl))bis(propane-1,2-dithiol) | 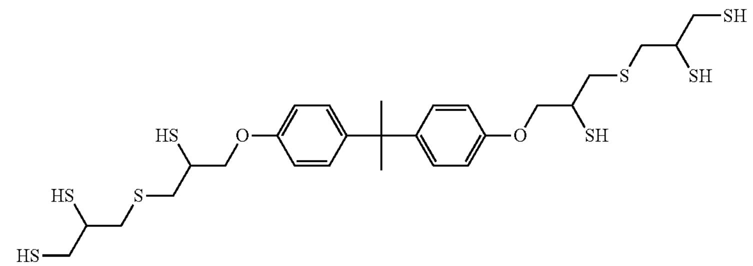 [SMILES: CC(C)(c1ccc(OCC(S)CSCC(S)CS)cc1)c1ccc(OCC(S)CSCC(S)CS)cc1] |
| 5,5'-(thiobis(propane-3,1-diyl))bis(1,3-bis(3-mercaptopropyl)-1,3,5-triazinane-2,4,6-trione) | 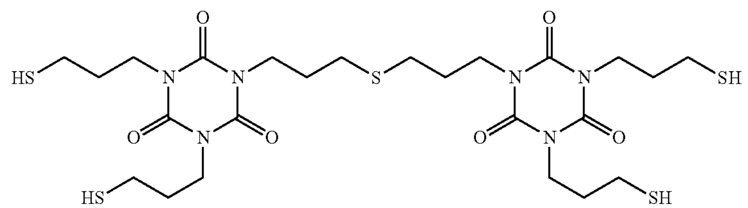 [SMILES: O=c1n(CCCS)c(=O)n(CCCSCCCn2c(=O)n(CCCS)c(=O)n(CCCS)c2=O)c(=O)n1CCCS] |
| 5,5'-((((5-(3-mercaptopropyl)-2,4,6-trioxo-1,3,5-triazinane-1,3-diyl)bis(propane-3,1-diyl))bis(sulfanediyl))bis(propane-3,1-diyl))bis(1,3-bis(3-mercaptopropyl)-1,3,5-triazinane-2,4,6-trione) | |

Poly(Alkylene Oxide)

In some embodiments, the poly(alkylene oxide) comprises at least one functional group attached to the poly(alkylene oxide) backbone. In some embodiments, the poly(alkylene oxide) is a poly(alkylene oxide) that comprises one functional group attached to the poly(alkylene oxide) backbone.

In some embodiments, the at least one functional group is an acrylate group, a methacrylate group, an acrylamide group, an isocyanate group, an alkene group, or a glycidyl ether group.

In some embodiments, the poly(alkylene oxide) is a mixture of a functional group terminated poly(alkylene oxide), a copolymer of alkylene oxides, and combinations thereof. In some embodiments, the functional group terminated poly(alkylene oxide) comprises a copolymer of alkylene oxides. In some embodiments, the copolymer is a random copolymer or a block copolymer. In some embodiments, the block copolymer is a diblock copolymer or a triblock copolymer. In some embodiments, the copolymer is based on a propylene oxide (PO), an ethylene oxide (EO), or a mixture of PO and EO. In some embodiments, the copolymer is a mixture of PO and EO.

In some embodiments, the poly(alkylene oxide) comprises a random copolymer of ethylene oxide and propylene oxide, a poly(ethylene oxide)-poly(propylene oxide) diblock copolymer, a poly(ethylene oxide)-poly(propylene oxide)-poly(ethylene oxide) triblock copolymer, a poly(propylene oxide)-poly(ethylene oxide)-poly(propylene oxide) triblock copolymer, or combinations thereof.

In some embodiments, the poly(alkylene oxide) comprises a copolymer of PO and EO. In some embodiments, the ratio of ethylene oxide groups to propylene oxide groups is sufficiently high so that the poly(alkylene oxide) ligand has a high degree of hydrophilicity. In some embodiments, the ratio of ethylene oxide groups to propylene oxide groups is low enough that the ligand has the desired resiliency. In some embodiments, the ratio of ethylene oxide groups: propylene oxide groups is between about 15:1 and about 1:15, about 15:1 and about 1:10, about 15:1 and about 1:5, about 10:1 and 1:15, about 10:1 and 1:10, about 10:1 and 1:5, about 5:1 and 1:15, about 5:1 and 1:10, or about 5:1 and 1:5.

In some embodiments, the poly(alkylene oxide) has the structure of formula V:

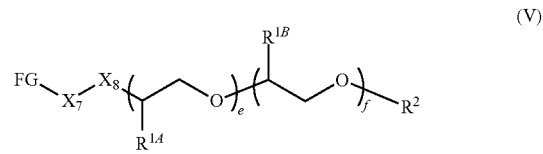

(V)

wherein:
FG is an acrylate group, a methacrylate group, an acrylamide group, an isocyanate group, an alkene group, or a glycidyl ether group;
$X_7$ is a bond or $C_{1-12}$ alkylene;
$X_8$ is a bond, —O—, —C(=O)—O—, or —C(=O)—N—;
$R^{1A}$ and $R^{1B}$ independently are H or $C_{1-20}$ alkyl;
e is 1 to 100;
f is 0 to 100; and
$R^2$ is $C_{1-20}$ alkyl or $C_{1-20}$ alkoxy.

In some embodiments, FG is an acrylate group. In some embodiments, FG is a methacrylate group. In some embodiments, FG is an acrylamide group. In some embodiments, FG is an isocyanate group. In some embodiments, FG is an alkene group. In some embodiments, FG is a glycidyl ether group. In some embodiments, FG is —O—C(=O)—CH=CH$_2$. In some embodiments, FG is —O—C(=O)—C(CH$_3$)=CH$_2$. In some embodiments, FG is —N—C(=O)—CH=CH$_2$. In some embodiments, FG is —N=C=O. In some embodiments, FG is —CH=CH$_2$. In some embodiments, FG is

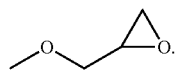

In some embodiments, X$_7$ is a bond. In some embodiments, X$_7$ is C$_{1-12}$ alkylene.

In some embodiments, X$_8$ is a bond. In some embodiments, X$_8$ is —O—. In some embodiments, X$_8$ is —OC(=O)—. In some embodiments, X$_8$ is amido.

In some embodiments, R$^{1A}$ is H. In some embodiments, R$^{1A}$ is C$_{1-20}$ alkyl. In some embodiments, R$^{1A}$ is C$_{1-10}$ alkyl. In some embodiments, R$^{1A}$ is C$_{1-5}$ alkyl. In some embodiments, R$^{1A}$ is —CH$_3$.

In some embodiments, R$^{1B}$ is H. In some embodiments, R$^{1B}$ is C$_{1-20}$ alkyl. In some embodiments, R$^{1B}$ is C$_{1-10}$ alkyl. In some embodiments, R$^{1B}$ is C$_{1-5}$ alkyl. In some embodiments, R$^{1B}$ is —CH$_3$.

In some embodiments, R$^{1A}$ is H and R$^{1B}$ is —CH$_3$. In some embodiments, R$^{1A}$ is —CH$_3$ and R$^{1B}$ is H. In some embodiments, R$^{1A}$ is H and R$^{1B}$ is H. In some embodiments, R$^{1A}$ is —CH$_3$ and R$^{1B}$ is —CH$_3$.

In some embodiments, e is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, e is 10 to 50. In some embodiments, e is 10 to 20.

The values for e are to be understood as modified by the word "about." Therefore, a value of e=1 is understood to mean e=1±0.1. For example, a value of e=1 is understood to mean 0.9 to 1.1.

In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, f is 1 to 30. In some embodiments, f is 1 to 10.

The values for f are to be understood as modified by the word "about." Therefore, a value of f=1 is understood to mean f=1±0.1. For example, a value of f=1 is understood to mean 0.9 to 1.1.

In some embodiments, the ratio of e to f is between about 15:1 and about 1:15, about 15:1 and about 1:10, about 15:1 and about 1:5, about 10:1 and about 1:15, about 10:1 and about 1:10, about 10:1 and about 1:5, about 5:1 and about 1:15, about 5:1 and about 1:10, or about 5:1 and about 1:5.

In some embodiments, R$^2$ is C$_{1-20}$ alkyl. In some embodiments, R$^2$ is C$_{1-10}$ alkyl. In some embodiments, R$^2$ is C$_{1-5}$ alkyl. In some embodiments, R$^2$ is —CH$_2$CH$_3$. In some embodiments, R$^2$ is —CH$_3$.

In some embodiments, wherein FG is —O—C(=O)—CH=CH$_2$, and X$_7$ and X$_8$ are bonds in formula V, the poly(alkylene oxide) has the structure of formula VI:

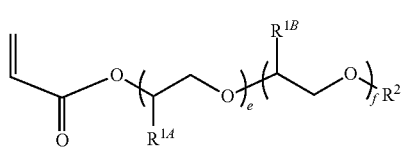

wherein:

R$^{1A}$ and R$^{1B}$ independently are H or C$_{1-20}$ alkyl;

e is 1 to 100;

f is 0 to 100; and

R$^2$ is C$_{1-20}$ alkyl or C$_{1-20}$ alkoxy.

In some embodiments, e is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100.

In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100.

In some embodiments, the ratio of e to f is between about 15:1 and about 1:15, about 15:1 and about 1:10, about 15:1 and about 1:5, about 10:1 and about 1:15, about 10:1 and about 1:10, about 10:1 and about 1:5, about 5:1 and about 1:15, about 5:1 and about 1:10, or about 5:1 and 1:5.

In some embodiments, R$^{1A}$ is H. In some embodiments, R$^{1A}$ is C$_{1-20}$ alkyl. In some embodiments, R$^{1A}$ is C$_{1-10}$ alkyl. In some embodiments, R$^{1A}$ is C$_{1-5}$ alkyl. In some embodiments, R$^{1A}$ is —CH$_3$.

In some embodiments, R$^{1B}$ is H. In some embodiments, R$^{1B}$ is C$_{1-20}$ alkyl. In some embodiments, R$^{1B}$ is C$_{1-10}$ alkyl. In some embodiments, R$^{1B}$ is C$_{1-5}$ alkyl. In some embodiments, R$^{1B}$ is —CH$_3$.

In some embodiments, R$^2$ is C$_{1-20}$ alkyl. In some embodiments, R$^2$ is C$_{1-10}$ alkyl. In some embodiments, R$^2$ is C$_{1-5}$ alkyl. In some embodiments, R$^2$ is —CH$_2$CH$_3$. In some embodiments, R$^2$ is —CH$_3$.

In some embodiments, wherein FG is —O—C(=O)—CH=CH$_2$, X$_7$ and X$_8$ are bonds, f is 0, and R$^2$ is —CH$_3$ in formula V, the poly(alkylene oxide) has the structure of formula VII:

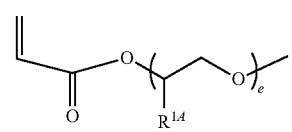

wherein:

R$^{1A}$ is H or C$_{1-20}$ alkyl; and e is 1 to 100.

In some embodiments, R$^{1A}$ is H. In some embodiments, R$^{1A}$ is C$_{1-20}$ alkyl. In some embodiments, R$^{1A}$ is C$_{1-10}$ alkyl. In some embodiments, R$^{1A}$ is C$_{1-5}$ alkyl. In some embodiments, R$^{1A}$ is —CH$_3$.

In some embodiments, e is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, e is 10 to 50. In some embodiments, e is 10 to 20. In some embodiments, e is 10. In some embodiments, e is 9. In some embodiments, e is 6.

Polythiol Ligand

In some embodiments, the polythiol ligand has formula I:

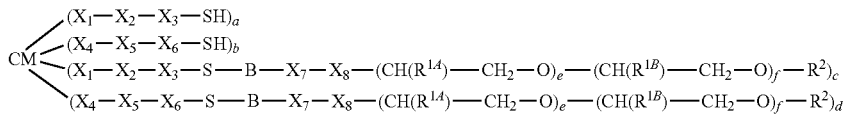

wherein:
CM is a central moiety;
$X_1$ is a bond, —C(=O)—, a $C_{1-10}$ alkylene, or a $C_{2-10}$ heteroalkylene;
$X_2$ is a bond, —C(=O)—, a $C_{1-10}$ alkylene, or a $C_{2-10}$ heteroalkylene;
$X_3$ is a bond, —C(=O)—, a $C_{1-10}$ alkylene, or a $C_{2-10}$ heteroalkylene;
$X_4$ is a bond, —C(=O)—, a $C_{1-10}$ alkylene, or a $C_{2-10}$ heteroalkylene;
$X_5$ is a bond, —C(=O)—, a $C_{1-10}$ alkylene, or a $C_{2-10}$ heteroalkylene;
$X_6$ is a bond, —C(=O)—, a $C_{1-10}$ alkylene, or a $C_{2-10}$ heteroalkylene;
B is —CH$_2$—CH$_2$—C(=O)—O—, —CH$_2$—C(CH$_3$)$_2$—C(=O)—O—, —CH$_2$—CH(CH$_3$)—C(=O)—NH—, —C(=O)—NH—, —CH$_2$—CH$_2$—, or —CH$_2$—CH(OH)—CH$_2$—O—;
$X_7$ is a bond or $C_{1-12}$ alkylene;
$X_8$ is a bond, —O—, —C(=O)—O—, or —C(=O)—N—;
$R^{1A}$ and $R^{1B}$ independently are H or $C_{1-20}$ alkyl;
$R^2$ is $C_{1-20}$ alkyl or $C_{1-20}$ alkoxy
a is 2 to 10;
b is 0 to 10;
c is 2 to 10;
d is 0 to 10;
e is 1 to 100; and
f is 0 to 100;
wherein a+b+c+d comprises a value within a range of 4 to 40.

In some embodiments, CM is an alkane, 1,3,5-triazine, pentaerythritol, 1,3,5-triazine-2,4,6-trione, trimethylolpropane, or (propane-2,2-diylbis(4,1-phenylene))bis(λ'-oxy). In some embodiments, CM is propane.

In some embodiments, $X_1$ is a bond. In some embodiments, $X_1$ is —C(=O)—. In some embodiments, $X_1$ is a substituted or unsubstituted $C_{1-10}$ alkylene. In some embodiments, $X_1$ is an unsubstituted $C_{1-10}$ alkylene. In some embodiments, $X_1$ is a substituted $C_{1-10}$ alkylene. In some embodiments, $X_1$ is a substituted or unsubstituted $C_{1-10}$ heteroalkylene. In some embodiments, $X_1$ is an unsubstituted $C_{1-10}$ heteroalkylene. In some embodiments, $X_1$ is a substituted $C_{1-10}$ heteroalkylene. In some embodiments, the substituent on $X_1$ is a —SH.

In some embodiments, $X_2$ is a bond. In some embodiments, $X_2$ is —C(=O)—. In some embodiments, $X_2$ is a substituted or unsubstituted $C_{1-10}$ alkylene. In some embodiments, $X_2$ is an unsubstituted $C_{1-10}$ alkylene. In some embodiments, $X_2$ is a substituted $C_{1-10}$ alkylene. In some embodiments, $X_2$ is a substituted or unsubstituted $C_{1-10}$ heteroalkylene. In some embodiments, $X_2$ is an unsubstituted $C_{1-10}$ heteroalkylene. In some embodiments, $X_2$ is a substituted $C_{1-10}$ heteroalkylene. In some embodiments, the substituent on $X_2$ is a —SH.

In some embodiments, $X_3$ is a bond. In some embodiments, $X_3$ is —C(=O)—. In some embodiments, $X_3$ is a substituted or unsubstituted $C_{1-10}$ alkylene. In some embodiments, $X_3$ is an unsubstituted $C_{1-10}$ alkylene. In some embodiments, $X_3$ is a substituted $C_{1-10}$ alkylene. In some embodiments, $X_3$ is a substituted or unsubstituted $C_{1-10}$ heteroalkylene. In some embodiments, $X_3$ is an unsubstituted $C_{1-10}$ heteroalkylene. In some embodiments, $X_3$ is a substituted $C_{1-10}$ heteroalkylene. In some embodiments, the substituent on $X_3$ is a —SH.

In some embodiments, $X_4$ is a bond. In some embodiments, $X_4$ is —C(=O)—. In some embodiments, $X_4$ is a substituted or unsubstituted $C_{1-10}$ alkylene. In some embodiments, $X_4$ is an unsubstituted $C_{1-10}$ alkylene. In some embodiments, $X_4$ is a substituted $C_{1-10}$ alkylene. In some embodiments, $X_4$ is a substituted or unsubstituted $C_{1-10}$ heteroalkylene. In some embodiments, $X_4$ is an unsubstituted $C_{1-10}$ heteroalkylene. In some embodiments, $X_4$ is a substituted $C_{1-10}$ heteroalkylene. In some embodiments, the substituent on $X_4$ is a —SH.

In some embodiments, $X_5$ is a bond. In some embodiments, $X_5$ is —C(=O)—. In some embodiments, $X_5$ is a substituted or unsubstituted $C_{1-10}$ alkylene. In some embodiments, $X_5$ is an unsubstituted $C_{1-10}$ alkylene. In some embodiments, $X_5$ is a substituted $C_{1-10}$ alkylene. In some embodiments, $X_5$ is a substituted or unsubstituted $C_{1-10}$ heteroalkylene. In some embodiments, $X_5$ is an unsubstituted $C_{1-10}$ heteroalkylene. In some embodiments, $X_5$ is a substituted $C_{1-10}$ heteroalkylene. In some embodiments, the substituent on $X_5$ is a —SH.

In some embodiments, $X_6$ is a bond. In some embodiments, $X_1$ is —C(=O)—. In some embodiments, $X_6$ is a substituted or unsubstituted $C_{1-10}$ alkylene. In some embodiments, $X_6$ is an unsubstituted $C_{1-10}$ alkylene. In some embodiments, $X_6$ is a substituted $C_{1-10}$ alkylene. In some embodiments, $X_6$ is a substituted or unsubstituted $C_{1-10}$ heteroalkylene. In some embodiments, $X_6$ is an unsubstituted $C_{1-10}$ heteroalkylene. In some embodiments, $X_6$ is a substituted $C_{1-10}$ heteroalkylene. In some embodiments, the substituent on $X_6$ is a —SH.

In some embodiments, B is —CH$_2$—CH$_2$—C(=O)—O—. In some embodiments, B is —CH$_2$—CH(CH$_3$)—C(=O)—O—. In some embodiments, B is —CH$_2$—CH$_2$—C(=O)—N—. In some embodiments, B is —C(=O)—NH—. In some embodiments, B is —CH$_2$—CH$_2$—. In some embodiments, B is —CH$_2$—CH(OH)—CH$_2$—O—. In some embodiments, B is —CH$_2$—CH(OH)—.

In some embodiments, $X_7$ is a bond. In some embodiments, $X_7$ is a substituted or unsubstituted $C_{1-12}$ alkylene. In some embodiments, $X_7$ is an unsubstituted $C_{1-12}$ alkylene. In some embodiments, $X_7$ is a substituted $C_{1-12}$ alkylene.

In some embodiments, $X_8$ is a bond. In some embodiments, $X_8$ is —O—. In some embodiments, $X_8$ is —C(=O)—O—. In some embodiments, $X_8$ is —C(=O)—N—.

In some embodiments, $R^{1A}$ is H. In some embodiments, $R^{1A}$ is $C_{1-20}$ alkyl. In some embodiments, $R^{1A}$ is $C_{1-10}$ alkyl. In some embodiments, $R^{1A}$ is $C_{1-5}$ alkyl. In some embodiments, $R^{1A}$ is —CH$_3$.

In some embodiments, $R^{1B}$ is H. In some embodiments, $R^{1B}$ is $C_{1-20}$ alkyl. In some embodiments, $R^{1B}$ is $C_{1-10}$ alkyl. In some embodiments, $R^{1B}$ is $C_{1-5}$ alkyl. In some embodiments, $R^{1B}$ is —$CH_3$.

In some embodiments, $R^2$ is $C_{1-20}$ alkyl. In some embodiments, $R^2$ is $C_{1-10}$ alkyl. In some embodiments, $R^2$ is $C_{1-5}$ alkyl. In some embodiments, $R^2$ is —$CH_2CH_3$. In some embodiments, $R^2$ is —$CH_3$.

In some embodiments, a is between 2 and 10. In some embodiments, a is between 2 and 10, 2 and 8, 2 and 6, 2 and 4, 2 and 3, 3 and 10, 3 and 8, 3 and 6, 3 and 4, 4 and 10, 4 and 8, 4 and 6, 6 and 10, 6 and 8, or 8 and 10. In some embodiments, a is 3. In some embodiments, a is 4. In some embodiments, a is 5. In some embodiments, a is 6.

In some embodiments, b is between 0 and 10. In some embodiments, b is between 1 and 10, 1 and 8, 1 and 6, 1 and 4, 1 and 3, 2 and 10, 2 and 8, 2 and 6, 2 and 4, 2 and 3, 3 and 10, 3 and 8, 3 and 6, 3 and 4, 4 and 10, 4 and 8, 4 and 6, 6 and 10, 6 and 8, or 8 and 10. In some embodiments, b is 3. In some embodiments, b is 4. In some embodiments, b is 5. In some embodiments, b is 6.

In some embodiments, c is between 2 and 10. In some embodiments, a is between 2 and 10, 2 and 8, 2 and 6, 2 and 4, 2 and 3, 3 and 10, 3 and 8, 3 and 6, 3 and 4, 4 and 10, 4 and 8, 4 and 6, 6 and 10, 6 and 8, or 8 and 10. In some embodiments, c is 3. In some embodiments, c is 4. In some embodiments, c is 5. In some embodiments, c is 6.

In some embodiments, d is between 0 and 10. In some embodiments, b is between 1 and 10, 1 and 8, 1 and 6, 1 and 4, 1 and 3, 2 and 10, 2 and 8, 2 and 6, 2 and 4, 2 and 3, 3 and 10, 3 and 8, 3 and 6, 3 and 4, 4 and 10, 4 and 8, 4 and 6, 6 and 10, 6 and 8, or 8 and 10. In some embodiments, d is 3. In some embodiments, d is 4. In some embodiments, d is 5. In some embodiments, d is 6.

In some embodiments, e is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100.

In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100.

In some embodiments, wherein b is 0 and d is 0 in formula I, the polythiol ligand has the structure of formula IV:

(II)

wherein:
CM is a central moiety;
$X_1$ is a bond, —C(=O)—, a $C_{1-10}$ alkylene, or a $C_{2-10}$ heteroalkylene;
$X_2$ is a bond, —C(=O)—, a $C_{1-10}$ alkylene, or a $C_{2-10}$ heteroalkylene;
$X_3$ is a bond, —C(=O)—, a $C_{1-10}$ alkylene, or a $C_{2-10}$ heteroalkylene;
B is —$CH_2$—$CH_2$—C(=O)—O—, —$CH_2$—C($CH_3$)$_2$—C(=O)—O—, —$CH_2$—CH($CH_3$)—C(=O)—NH—, —C(=O)—NH—, —$CH_2$—$CH_2$—, or —$CH_2$—CH(OH)—$CH_2$—O—;

$X_7$ is a bond or $C_{1-12}$ alkylene;
$X_8$ is a bond, —O—, —C(=O)—O—, or —C(=O)—N—;
$R^{1A}$ and $R^{1B}$ independently are H or $C_{1-20}$ alkylene;
$R^2$ is $C_{1-20}$ alkylene or $C_{1-20}$ alkoxy;
a is 2 to 10;
c is 2 to 10;
e is 1 to 100; and
f is 0 to 100;
wherein a +c≥4 and ≤20.

In some embodiments, CM is an alkane, 1,3,5-triazine, pentaerythritol, 1,3,5-triazine-2,4,6-trione, trimethylolpropane, or (propane-2,2-diylbis(4,1-phenylene))bis(λ'-oxy). In some embodiments, CM is propane.

In some embodiments, $X_1$ is a bond. In some embodiments, $X_1$ is —C(=O)—. In some embodiments, $X_1$ is a substituted or unsubstituted $C_{1-10}$ alkylene. In some embodiments, $X_1$ is an unsubstituted $C_{1-10}$ alkylene. In some embodiments, $X_1$ is a substituted $C_{1-10}$ alkylene. In some embodiments, $X_1$ is a substituted or unsubstituted $C_{1-10}$ heteroalkylene. In some embodiments, $X_1$ is an unsubstituted $C_{1-10}$ heteroalkylene. In some embodiments, $X_1$ is a substituted $C_{1-10}$ heteroalkylene. In some embodiments, the substituent on $X_1$ is a —SH.

In some embodiments, $X_2$ is a bond. In some embodiments, $X_2$ is —C(=O)—. In some embodiments, $X_2$ is a substituted or unsubstituted $C_{1-10}$ alkylene. In some embodiments, $X_2$ is an unsubstituted $C_{1-10}$ alkylene. In some embodiments, $X_2$ is a substituted $C_{1-10}$ alkylene. In some embodiments, $X_2$ is a substituted or unsubstituted $C_{1-10}$ heteroalkylene. In some embodiments, $X_2$ is an unsubstituted $C_{1-10}$ heteroalkylene. In some embodiments, $X_2$ is a substituted $C_{1-10}$ heteroalkylene. In some embodiments, the substituent on $X_2$ is a —SH.

In some embodiments, $X_3$ is a bond. In some embodiments, $X_3$ is —C(=O)—. In some embodiments, $X_3$ is a substituted or unsubstituted $C_{1-10}$ alkylene. In some embodiments, $X_3$ is an unsubstituted $C_{1-10}$ alkylene. In some embodiments, $X_3$ is a substituted $C_{1-10}$ alkylene. In some embodiments, $X_3$ is a substituted or unsubstituted $C_{1-10}$ heteroalkylene. In some embodiments, $X_3$ is an unsubstituted $C_{1-10}$ heteroalkylene. In some embodiments, $X_3$ is a substituted $C_{1-10}$ heteroalkylene. In some embodiments, the substituent on $X_3$ is a —SH.

In some embodiments, B is —$CH_2$—$CH_2$—C(=O)—O—. In some embodiments, B is —$CH_2$—CH($CH_3$)—C(=O)—O—. In some embodiments, B is —$CH_2$—$CH_2$—C(=O)—N—. In some embodiments, B is —C(=O)—NH—. In some embodiments, B is —$CH_2$—$CH_2$—. In some embodiments, B is —$CH_2$—CH(OH)—$CH_2$—O—. In some embodiments, B is —$CH_2$—CH(OH)—.

In some embodiments, $X_7$ is a bond. In some embodiments, $X_7$ is a substituted or unsubstituted $C_{1-12}$ alkylene. In some embodiments, $X_7$ is an unsubstituted $C_{1-12}$ alkylene. In some embodiments, $X_7$ is a substituted $C_{1-12}$ alkylene.

In some embodiments, $X_8$ is a bond. In some embodiments, $X_8$ is —O—. In some embodiments, $X_8$ is —C(=O)—O—. In some embodiments, $X_8$ is —C(=O)—N—.

In some embodiments, $R^{1A}$ is H. In some embodiments, $R^{1A}$ is $C_{1-20}$ alkyl. In some embodiments, $R^{1A}$ is $C_{1-10}$ alkyl. In some embodiments, $R^{1A}$ is $C_{1-5}$ alkyl. In some embodiments, $R^{1A}$ is —$CH_3$.

In some embodiments, $R^{1B}$ is H. In some embodiments, $R^{1B}$ is $C_{1-20}$ alkyl. In some embodiments, $R^{1B}$ is $C_{1-10}$ alkyl. In some embodiments, $R^{1B}$ is $C_{1-5}$ alkyl. In some embodiments, $R^{1B}$ is —$CH_3$.

In some embodiments, $R^2$ is $C_{1-20}$ alkyl. In some embodiments, $R^2$ is $C_{1-10}$ alkyl. In some embodiments, $R^2$ is $C_{1-5}$ alkyl. In some embodiments, $R^2$ is —$CH_2CH_3$. In some embodiments, $R^2$ is —$CH_3$.

In some embodiments, a is between 2 and 10. In some embodiments, a is between 2 and 10, 2 and 8, 2 and 6, 2 and 4, 2 and 3, 3 and 10, 3 and 8, 3 and 6, 3 and 4, 4 and 10, 4 and 8, 4 and 6, 6 and 10, 6 and 8, or 8 and 10. In some embodiments, a is 3. In some embodiments, a is 4. In some embodiments, a is 5. In some embodiments, a is 6.

In some embodiments, c is between 2 and 10. In some embodiments, a is between 2 and 10, 2 and 8, 2 and 6, 2 and 4, 2 and 3, 3 and 10, 3 and 8, 3 and 6, 3 and 4, 4 and 10, 4 and 8, 4 and 6, 6 and 10, 6 and 8, or 8 and 10. In some embodiments, c is 3. In some embodiments, c is 4. In some embodiments, c is 5. In some embodiments, c is 6.

In some embodiments, e is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100.

In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100. In some embodiments, f is 1 to 100, 1 to 50, 1 to 20, 1 to 10, 1 to 5, 5 to 100, 5 to 50, 5 to 20, 5 to 10, 10 to 100, 10 to 50, 10 to 20, 20 to 100, 20 to 50, or 50 to 100.

Preparation of Polythiol Ligands

Figure 2:
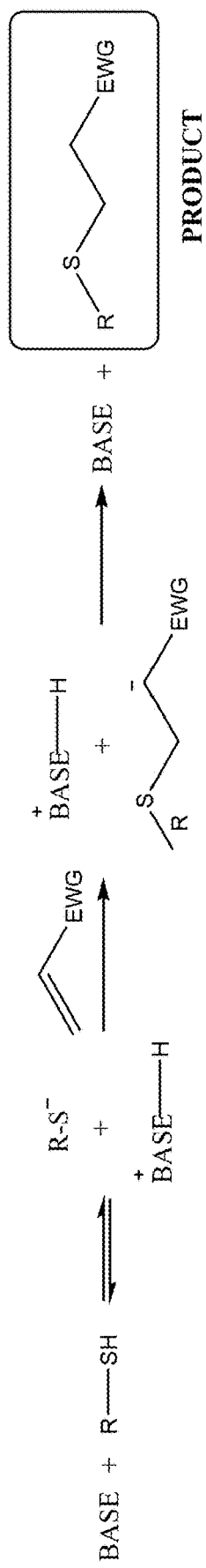
FIG. 2 is a schematic depicting the base-catalyzed Michael addition reaction where EWG is an electron-withdrawing group.

The polythiol ligands can be prepared by a base-catalyzed Michael addition reaction of at least one thiol on the polythiol and at least one functional group on the poly(alkylene oxide), wherein the at least one functional group is an acrylate, a methacrylate, or an acrylamide. An example of the Michael reaction is 1,4-addition to an α,β-unsaturated carbonyl compound as shown in FIG. 2. See Chatani, S., et al., "Relative reactivity and selectivity of vinyl sulfones and acrylates towards the thiol-Michael addition reaction and polymerization," Polym. Chem. 4:1048-1055 (2013).

In some embodiments, the base catalyst is selected from the group consisting of N,N-dimethylformamide, triethylamine, pyridine, tetrabutylammonium chloride, or N-methyl imidazole. In some embodiments, the base catalyst is triethylamine.

In some embodiments, the reaction is carried out at a temperature between about −20° C. and about 100° C. In some embodiments, the base-catalyzed reaction is carried out at a temperature between about −20° C. and about 100° C., about −20° C. and about 80° C., about −20° C. and about 60° C., about −20° C. and about 40° C., about −20° C. and about 20° C., about 20° C. and about 100° C., about 20° C. and about 80° C., about 20° C. and about 60° C., about 20° C. and about 40° C., about 40° C. and about 100° C., about 40° C. and about 80° C., about 40° C. and about 60° C., about 60° C. and about 100° C., about 60° C. and about 80° C., or about 80° C. and about 100° C. In some embodiments, the reaction is carried out at a temperature between about 60° C. and about 100° C.

In some embodiments, the polythiol ligand is prepared from a polythiol and an acrylate-terminated poly(alkylene oxide) by the reaction shown in SCHEME 1.

SCHEME 1

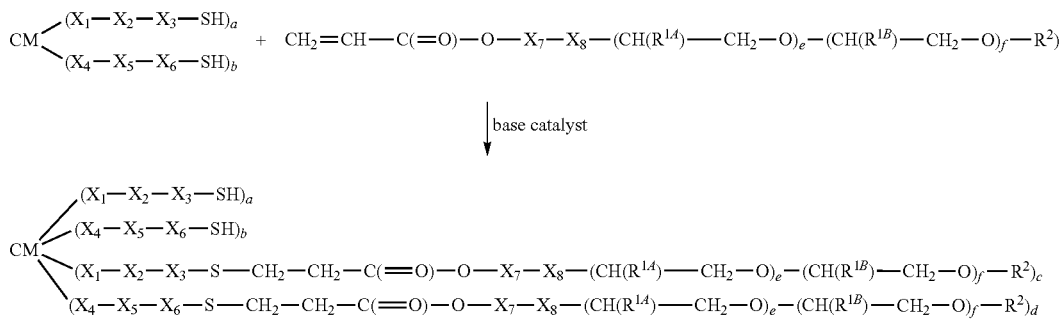

In some embodiments, the polythiol ligand is prepared from a polythiol and a methacrylate-terminated poly(alkylene oxide) by the reaction shown in SCHEME 2.

SCHEME 2

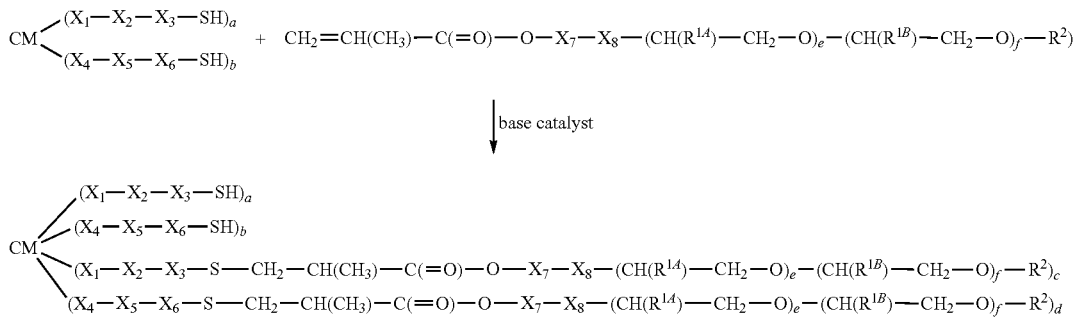

In some embodiments, the polythiol ligand is prepared from a polythiol and an acrylamide-terminated poly(alkylene oxide) by the reaction shown in SCHEME 3.

SCHEME 3

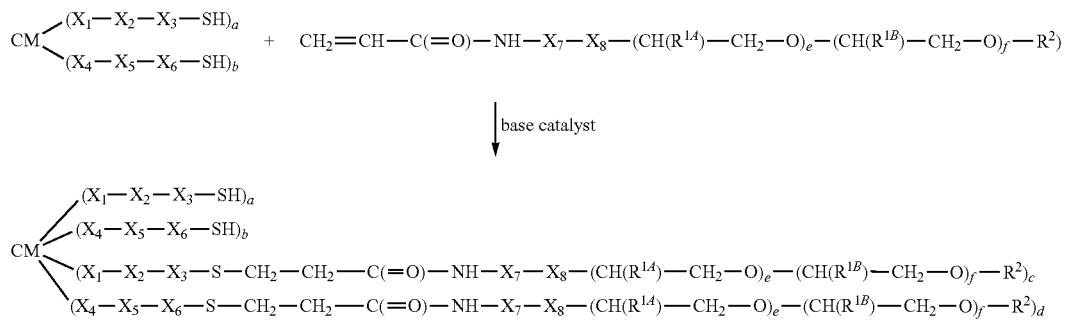

The polythiol ligands can also be prepared by a base-catalyzed reaction of at least one thiol on the polythiol and at least one functional group on the poly(alkylene oxide), wherein the at least one functional group is an isocyanate or a glycidyl ether. See Nguyen, L.-T. T, et al., *Polym. Chem.* 4:5527-5536 (2013).

In some embodiments, the base catalyst is selected from the group consisting of N,N-dimethylformamide, triethylamine, pyridine, tetrabutylammonium chloride, or N-methyl imidazole. In some embodiments, the base catalyst is triethylamine.

In some embodiments, the reaction is carried out at a temperature between about −20° C. and about 100° C. In some embodiments, the base-catalyzed reaction is carried out at a temperature between about −20° C. and about 100° C., about −20° C. and about 80° C., about −20° C. and about 60° C., about −20° C. and about 40° C., about −20° C. and about 20° C., about 20° C. and about 100° C., about 20° C. and about 80° C., about 20° C. and about 60° C., about 20° C. and about 40° C., about 40° C. and about 100° C., about 40° C. and about 80° C., about 40° C. and about 60° C., about 60° C. and about 100° C., about 60° C. and about 80° C., or about 80° C. and about 100° C. In some embodiments, the reaction is carried out at a temperature between about 60° C. and about 100° C.

In some embodiments, the polythiol ligand is prepared from a polythiol and an isocyanate-terminated poly(alkylene oxide) by the reaction shown in SCHEME 4.

SCHEME 4

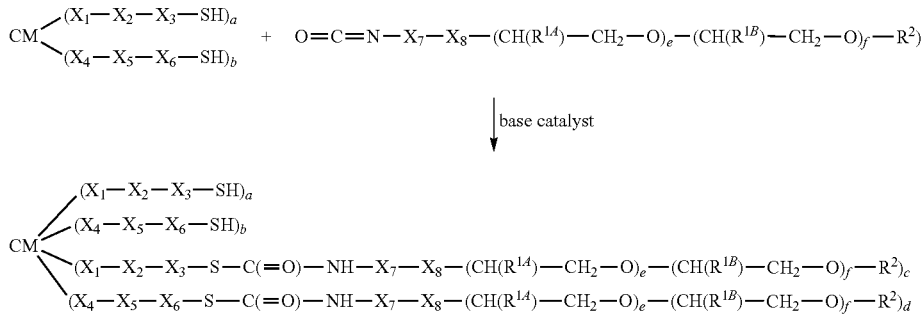

In some embodiments, the polythiol ligand is prepared from a polythiol and a glyidyl ether-terminated poly(alkylene oxide) by the reaction shown in SCHEME 5.

SCHEME 5

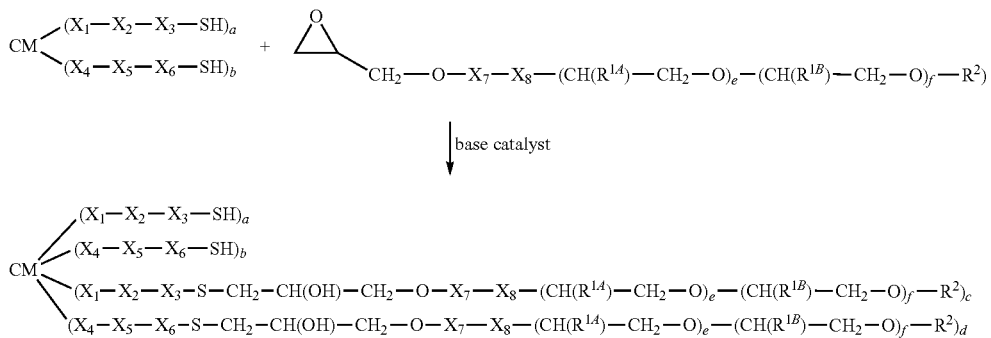

The polythiol ligands can also be prepared by a radical mediated reaction of at least one thiol on the polythiol and at least one functional group on the poly(alkylene oxide), wherein the at least one functional group is an alkene. See Nguyen, L.-T. T, et al., *Polym. Chem.* 4:5527-5536 (2013).

In some embodiments, the radical mediator is a photoinitiator such as dimethoxy-2-phenylacetophenone.

In some embodiments, the polythiol ligand is prepared from a polythiol and an alkene-terminated poly(alkylene oxide) by the reaction shown in SCHEME 6.

Ligand Exchange

In some embodiments, the present invention is directed to a method for exchanging ligands on nanostructures. In some embodiments, the present invention is directed to a method of replacing a first ligand on a nanostructure with a second ligand. In some embodiments, the second ligand is a polythiol ligand. In some embodiments, the nanostructure is a quantum dot.

In some embodiments, a first ligand on a nanostructure dot is exchanged with a polythiol ligand. Thiol groups

SCHEME 6

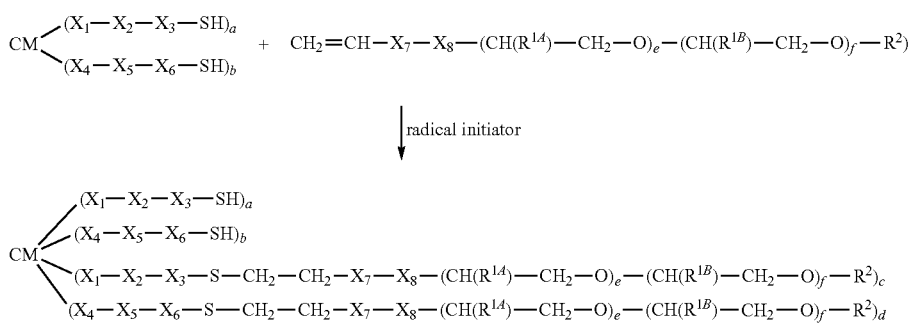

displace the native hydrophobic ligands of the nanostructure and afford a stable anchoring of the ligand onto the nanocrystal surface. In some embodiments, the nanostructure is a quantum dot.

In some embodiments, the present invention is directed to a method of replacing a first ligand on a nanostructure with a second ligand comprising:

admixing a reaction mixture comprising a population of nanostructures having a first ligand bound to the nanostructure and a second ligand, wherein the second ligand is a polythiol ligand, such that the second ligand displaces the first ligand and becomes bound to the nanostructure.

In some embodiments, the nanostructure is a quantum dot.

In some embodiments, the first ligand is bound covalently to the nanostructure. In some embodiments, the first ligand is bound non-covalently to the nanostructure.

In some embodiments, the second ligand becomes covalently bound to the nanostructure. In some embodiments, the second ligand becomes non-covalently bound to the nanostructure.

In some embodiments, the admixing is performed at a temperature between about 0° C. and about 200° C., about 0° C. and about 150° C., about 0° C. and about 100° C., about 0° C. and about 80° C., about 20° C. and about 200° C., about 20° C. and about 150° C., about 20° C. and about 100° C., about 20° C. and about 80° C., about 50° C. and about 200° C., about 50° C. and about 150° C., about 50° C. and about 100° C., about 50° C. and about 80° C., about 80° C. and about 200° C., about 80° C. and about 150° C., about 80° C. and about 100° C., about 100° C. and about 200° C., about 100° C. and about 150° C., or about 150° C. and about 200° C. In some embodiments, the admixing is performed at a temperature between about 50° C. and about 100° C. In some embodiments, the admixing is performed at a temperature of about 80° C.

In some embodiments, the admixing is performed over a period of about 1 minute and about 6 hours, about 1 minute and about 2 hours, about 1 minute and about 1 hour, about 1 minute and about 40 minutes, about 1 minute and about 30 minutes, about 1 minute and about 20 minutes, about 1 minute and about 10 minutes, about 10 minutes and about 6 hours, about 10 minutes and about 2 hours, about 10 minutes and about 1 hour, about 10 minutes and about 40 minutes, about 10 minutes and about 30 minutes, about 10 minutes and about 20 minutes, about 20 minutes and about 6 hours, about 20 minutes and about 2 hours, about 20 minutes and about 1 hour, about 20 minutes and about 40 minutes, about 20 minutes and about 30 minutes, about 30 minutes and about 6 hours, about 30 minutes and about 2 hours, about 30 minutes and about 1 hour, about 30 minutes and about 40 minutes, about 40 minutes and about 6 hours, about 40 minutes and about 2 hours, about 40 minutes and about 1 hour, about 1 hour and about 6 hours, about 1 hour and about 2 hours, or about 2 hours and about 6 hours. In some embodiments, the admixing is performed over a period of about 40 minutes and about 2 hours. In some embodiments, the admixing is performed over a period of about 1 hour.

In some embodiments, the reaction mixture further comprises a solvent. In some embodiments, the solvent is selected from the group consisting of chloroform, acetone, butanone, ethylene glycol monoethyl ether, ethylene glycol monopropyl ether, ethylene glycol monobutyl ether, diethylene glycol diethyl ether, methyl ethyl ketone, methyl isobutyl ketone, monomethyl ether glycol ester, gamma-butyrolactone, methylacetic-3-ethyl ether, butyl carbitol, butyl carbitol acetate, propanediol monomethyl ether, propanediol monomethyl ether acetate, cyclohexane, toluene, xylene, isopropyl alcohol, propylene glycol methyl ether acetate, hexanediol methacrylate, and combinations thereof. In some embodiments, the solvent is propylene glycol methyl ether acetate.

Optical density is a measure of the absorption of a material at a particular wavelength and is given the formula:

$$OD=-\log_{10}*(I_{OUT}/I_{IN})$$

where:

$I_{OUT}$=the intensity of radiation passing through the cell; and $I_{IN}$=the intensity of radiation shining on the cell.

The optical density of a material can be measured using a UV-Vis spectrometer.

The ratio of the quantum dots to the polythiol ligand can be determined by measuring the optical density of a stock solution at a desired wavelength. For example, to achieve a quantum dot to polythiol ligand concentration ratio of 5.0 mg/mL/$OD_{460}$, 4.0 mL of a stock solution of quantum dots with an optical density of 10 (measured at a wavelength of 460 nm in a 1 cm path length cuvette) can be combined with 200 mg of a polythiol ligand. And, to achieve a quantum dot to polythiol ligand concentration ratio of 2.5 mg/mL/$OD_{460}$, 4.0 mL of a stock solution of quantum dots with an optical density of 10 (measured at a wavelength of 460 nm in a 1 cm path length cuvette) can be combined with 100 mg of a polythiol ligand.

In some embodiments, the concentration ratio of quantum dots to the polythiol ligand measured by optical density (at a wavelength between about 450 nm and about 600 nm) is between about 0.25 mg/mL and about 10 mg/mL, about 0.25 mg/mL and about 5 mg/mL, about 0.25 mg/mL and about 1 mg/mL, about 0.25 mg/mL and about 0.5 mg/mL, about 0.5 mg/mL and about 10 mg/mL, about 0.5 mg/mL and about 5 mg/mL, about 0.5 mg/mL and about 1 mg/mL, about 1 mg/mL and about 10 mg/mL, about 1 mg/mL and about 5 mg/mL, or about 5 mg/mL and about 10 mg/mL. In some embodiments, the concentration ratio of quantum dots to the polythiol ligand measured by optical density (at a wavelength of about 450 nm) is between about 0.25 mg/mL and about 10 mg/mL, about 0.25 mg/mL and about 5 mg/mL, about 0.25 mg/mL and about 1 mg/mL, about 0.25 mg/mL and about 0.5 mg/mL, about 0.5 mg/mL and about 10 mg/mL, about 0.5 mg/mL and about 5 mg/mL, about 0.5 mg/mL and about 1 mg/mL, about 1 mg/mL and about 10 mg/mL, about 1 mg/mL and about 5 mg/mL, or about 5 mg/mL and about 10 mg/mL. In some embodiments, the concentration ratio of quantum dots to the polythiol ligand measured by optical density (at a wavelength of about 450 nm) is between about 1 mg/mL and about 5 mg/mL.

In some embodiments, the ratio of quantum dots to the polythiol ligand measured by optical density (at a wavelength between about 600 nm and about 750 nm) is between about 0.25 mg/mL and about 10 mg/mL, about 0.25 mg/mL and about 5 mg/mL, about 0.25 mg/mL and about 1 mg/mL, about 0.25 mg/mL and about 0.5 mg/mL, about 0.5 mg/mL and about 10 mg/mL, about 0.5 mg/mL and about 5 mg/mL, about 0.5 mg/mL and about 1 mg/mL, about 1 mg/mL and about 10 mg/mL, about 1 mg/mL and about 5 mg/mL, or about 5 mg/mL and about 10 mg/mL.

The percentage of first ligands displaced by the polythiol ligand can be measured by $^1$H NMR. In some embodiments, the mole percentage of first ligands displaced by the polythiol ligand is between about 20% and about 100%, about 20% and about 80%, 20% and about 60%, about 20% and about 40%, about 25% and about 100%, about 25% and about 80%, about 25% and about 60%, about 25% and about 40%, about 30% and about 100%, about 30% and about 80%, about 30% and about 60%, about 30% and about 40%, about 40% and about 100%, about 40% and about 80%, about 40% and about 60%, about 60% and about 100%, about 60% and about 80%, or about 80% and about 100%.

The percentage of nanostructures in a population of nanostructures that comprise a polythiol ligand can be measured by $^1$H NMR. In some embodiments, the mole percentage of ligands in a population of nanostructures that comprise a polythiol ligand is between about 20% and about 100%, about 20% and about 80%, about 20% and about 60%, about 20% and about 40%, about 25% and about 100%, about 25% and about 80%, about 25% and about 60%, about 25% and about 40%, about 30% and about 100%, about 30% and about 80%, about 30% and about 60%, about 30% and about 40%, about 40% and about 100%, about 40% and about 80%, about 40% and about 60%, about 60% and about 100%, about 60% and about 80%, or about 80% and about 100%.

Increased Solubility

In some embodiments, the polythiol ligands are soluble in a polar solvent or a combination of solvents comprising at least one polar solvent. In some embodiments, nanostructures comprising polythiol ligands dispersed on the nanostructures are soluble in a polar solvent or a combination of solvents comprising at least one polar solvent.

A polythiol ligand is soluble in a polar solvent when at least 1 gram of the polythiol ligand dissolves in 1000 mL or less of the polar solvent at room temperature with agitation. The amount of polythiol ligand that dissolves can be determined by visual inspection.

In some embodiments, the polar solvent is selected from the group consisting of water, deuterium oxide, methanol, ethanol, acetone, methyl ethyl ketone, isopropanol, n-propanol, n-butanol, acetonitrile, dimethyl sulfoxide, deuterated dimethyl sulfoxide, dimethyl formamide, ethylene glycol, pyridine, diethylene glycol, benzonitrile, cyclohexanone, chloroform, ethyl acetate, propylene glycol methyl ether acetate, and dichloromethane.

Organic Resin

In some embodiments, the organic resin is a thermosetting resin or an ultraviolet (UV) curable resin. In some embodiments, the organic resin is cured with a method that facilitates roll-to-roll processing.

Thermosetting resins require curing in which they undergo an irreversible molecular cross-linking process which renders the resin infusible. In some embodiments, the thermosetting resin is an epoxy resin, a phenolic resin, a vinyl resin, a melamine resin, a urea resin, an unsaturated polyester resin, a polyurethane resin, an allyl resin, an acrylic resin, a polyamide resin, a polyamide-imide resin, a phenolamine condensation polymerization resin, a urea melamine condensation polymerization resin, or combinations thereof.

In some embodiments, the thermosetting resin is an epoxy resin. Epoxy resins are easily cured without evolution of volatiles or by-products by a wide range of chemicals. Epoxy resins are also compatible with most substrates and tend to wet surfaces easily. See Boyle, M. A., et al., "Epoxy Resins," Composites, Vol. 21, ASM Handbook, pages 78-89 (2001).

In some embodiments, the organic resin is a silicone thermosetting resin. In some embodiments, the silicone thermosetting resin is OE6630A or OE6630B (Dow Corning Corporation, Auburn, MI).

In some embodiments, a thermal initiator is used. In some embodiments, the thermal initiator is [2,2'-azobis(2-methylpropionitrile)] (AIBN) or benzoyl peroxide.

UV curable resins are polymers that cure and quickly harden when exposed to a specific light wavelength. In some embodiments, the UV curable resin is a resin having as a functional group a radical-polymerization group such as a (meth)acryloxy group, a vinyloxy group, a styryl group, or a vinyl group; or a cation-polymerizable group such as an epoxy group, a thioepoxy group, a vinyloxy group, or an oxetanyl group. In some embodiments, the UV curable resin is a polyester resin, a polyether resin, a (meth)acrylic resin, an epoxy resin, a urethane resin, an alkyd resin, a spiroacetal resin, a polybutadiene resin, or a polythiolpolyene resin.

In some embodiments, the UV curable resin is selected from the group consisting of isobornyl acrylate (IBOA), urethane acrylate, allyloxylated cyclohexyl diacrylate, bis(acryloxy ethyl)hydroxyl isocyanurate, bis(acryloxy neopentylglycol)adipate, bisphenol A diacrylate, bisphenol A dimethacrylate, 1,4-butanediol diacrylate, 1,4-butanediol dimethacrylate, 1,3-butyleneglycol diacrylate, 1,3-butyleneglycol dimethacrylate, dicyclopentanyl diacrylate, diethyleneglycol diacrylate, diethyleneglycol dimethacrylate, dipentaerythritol hexaacrylate, dipentaerythritol monohydroxy pentaacrylate, di(trimethylolpropane) tetraacrylate, ethyleneglycol dimethacrylate, glycerol methacrylate, 1,6-hexanediol diacrylate, neopentylglycol dimethacrylate, neopentylglycol hydroxypivalate diacrylate, pentaerythritol triacrylate, pentaerythritol tetraacrylate, phosphoric acid dimethacrylate, polyethyleneglycol diacrylate, polypropyleneglycol diacrylate, tetraethyleneglycol diacrylate, tetrabromobisphenol A diacrylate, triethyleneglycol divinylether, triglycerol diacrylate, trimethylolpropane triacrylate, tripropyleneglycol diacrylate, tris(acryloxyethyl)isocyanurate, phosphoric acid triacrylate, phosphoric acid diacrylate, acrylic acid propargyl ester, vinyl terminated polydimethylsiloxane, vinyl terminated diphenylsiloxane-dimethylsiloxane copolymer, vinyl terminated polyphenylmethylsiloxane, vinyl terminated trifluoromethylsiloxane-dimethylsiloxane copolymer, vinyl terminated diethylsiloxane-dimethylsiloxane copolymer, vinylmethylsiloxane, monomethacryloyloxypropyl terminated polydimethyl siloxane, monovinyl terminated polydimethyl siloxane, monoallyl-mono trimethylsiloxy terminated polyethylene oxide, and combinations thereof.

In some embodiments, the UV curable resin is a thiol-functionalized resin or polythiol-functionalized resin that can be cross-linked with an isocyanate, an epoxy, or an unsaturated compound under UV curing conditions.

In some embodiments, the polythiol-functionalized resin is pentaerythritol tetrakis(3-mercaptopropionate) (PTMP); trimethylol-propane tri(3-mercaptopropionate) (TMPMP); glycol di(3-mercapto-propionate) (GDMP); tris[25-(3-mercaptopropionyloxy)ethyl]isocyanurate (TEMPIC); di-pentaerythritol hexa(3-mercaptopropionate) (Di-PETMP); ethoxylated trimethylolpropane tri(3-mercaptopropionate) (ETTMP 1300 and ETTMP 700); polycaprolactone tetra(3-mercaptopropionate) (PCL4MP 1350); pentaerythritol tetramercaptoacetate (PETMA); trimethylol-propane trimercaptoacetate (TMPMA); or glycol dimercaptoacetate (GDMA). These compounds are sold under the trade name THIO-CURE® by Bruno Bock, Marschacht, Germany.

In some embodiments, the UV curable resin is a polythiol-functionalized resin. In some embodiments, the UV curable resin is a polythiol-functionalized compound selected from the group consisting of ethylene glycol bis (thioglycolate), ethylene glycol bis(3-mercaptopropionate), trimethylol propane tris (thioglycolate), trimethylol propane tris (3-mercaptopropionate), pentaerythritol tetrakis (thioglycolate), pentaerythritol tetrakis(3-mercaptopropionate) (PETMP), and combinations thereof. In some embodiments, the polythiol-functionalized resin is PETMP.

In some embodiments, the UV curable resin is a thiol-ene formulation comprising a polythiol-functionalized resin and 1,3,5-triallyl-1,3,5-triazine-2,4,6-(1H,3H,5H)-trione (TTT). In some embodiments, the UV curable resin is a thiol-ene formulation comprising PETMP and TTT.

In some embodiments, the UV curable resin further comprises a photoinitiator. A photoinitiator initiates the curing reaction of the photosensitive material during exposure to light. In some embodiments, the photoinitiator is acetophenone-based, benzoin-based, or thioxathenone-based.

In some embodiments, the photoinitiator is MINS-311RM (Minuta Technology Co., Ltd, Korea).

In some embodiments, the photoinitiator is IRGACURE 127, IRGACURE 184, IRGACURE 184D, IRGACURE 2022, IRGACURE 2100, IRGACURE 250, IRGACURE 270, IRGACURE 2959, IRGACURE 369, IRGACURE 369 EG, IRGACURE 379, IRGACURE 500, IRGACURE 651, IRGACURE 754, IRGACURE 784, IRGACURE 819, IRGACURE 819Dw, IRGACURE 907, IRGACURE 907 FF, IRGACURE Oxe01, IRGACURE TPO-L, IRGACURE 1173, IRGACURE 1173D, IRGACURE 4265, IRGACURE BP, or IRGACURE MBF (BASF Corporation, Wyandotte, MI). In some embodiments, the photoinitiator is TPO (2,4,6-trimethylbenzoyl-diphenyl-phosphine oxide) or MBF (methyl benzoylformate).

In some embodiments, the weight percentage of the organic resin in the nanostructure composition is between about 5% and about 50%, about 5% and about 40%, about 5% and about 30%, about 5% and about 20%, about 5% and about 10%, about 10% and about 50%, about 10% and about 40%, about 10% and about 30%, about 10% and about 20%, about 20% and about 50%, about 20% and about 40%, about 20% and about 30%, about 30% and about 50%, about 30% and about 40%, or about 40% and about 50%.

In some embodiments, the weight percentage of the organic resin in the nanostructure molded article is between about 0.01% and about 50%, about 0.01% and about 25%, about 0.01% and about 20%, about 0.01% and about 15%, about 0.01% and about 10%, about 0.01% and about 5%, about 0.01% and about 2%, about 0.01% and about 1%, about 1% and about 50%, about 1% and about 25%, about 1% and about 20%, about 1% and about 15%, about 1% and about 10%, about 1% and about 5%, about 1% and about 2%, about 2% and about 50%, about 2% and about 25%, about 2% and about 20%, about 2% and about 15%, about 2% and about 10%, about 2% and about 5%, 5% and about 50%, about 5% and about 25%, about 5% and about 20%, about 5% and about 15%, about 5% and about 10%, about 10% and about 50%, about 10% and about 25%, about 10% and about 20%, about 10% and about 15%, about 15% and about 50%, about 15% and about 25%, about 15% and about 20%, about 20% and about 50%, about 20% and about 25%, or about 25% and about 50%.

In some embodiments, if more than one organic resin is used, the organic resins are added together and mixed. In some embodiments, a first organic resin and a second organic resin are added together and mixed.

In some embodiments, a first organic resin is mixed with a second organic resin at an agitation rate of between about 100 rpm and about 10,000 rpm, about 100 rpm and about 5,000 rpm, about 100 rpm and about 3,000 rpm, about 100 rpm and about 1,000 rpm, about 100 rpm and about 500 rpm, about 500 rpm and about 10,000 rpm, about 500 rpm and about 5,000 rpm, about 500 rpm and about 3,000 rpm, about 500 rpm and about 1,000 rpm, about 1,000 rpm and about 10,000 rpm, about 1,000 rpm and about 5,000 rpm, about 1,000 rpm and about 3,000 rpm, about 3,000 rpm and about 10,000 rpm, about 3,000 rpm and about 10,000 rpm, or about 5,000 rpm and about 10,000 rpm.

In some embodiments, a first organic resin is mixed with a second organic resin for a time of between about 10 minutes and about 24 hours, about 10 minutes and about 20 hours, about 10 minutes and about 15 hours, about 10 minutes and about 10 hours, about 10 minutes and about 5 hours, about 10 minutes and about 1 hour, about 10 minutes and about 30 minutes, about 30 minutes and about 24 hours, about 30 minutes and about 20 hours, about 30 minutes and about 15 hours, about 30 minutes and about 10 hours, about 30 minutes and about 5 hours, about 30 minutes and about 1 hour, about 1 hour and about 24 hours, about 1 hour and about 20 hours, about 1 hour and about 15 hours, about 1 hour and about 10 hours, about 1 hour and about 5 hours, about 5 hours and about 24 hours, about 5 hours and about 20 hours, about 5 hours and about 15 hours, about 5 hours and about 10 hours, about 10 hours and about 24 hours, about 10 hours and about 20 hours, about 10 hours and about 15 hours, about 15 hours and about 24 hours, about 15 hours and about 20 hours, or about 20 hours and about 24 hours.

Making the Nanostructure Compositions

The present invention provides a method of making a nanostructure composition comprising admixing at least one population of nanostructures and at least one organic resin. In some embodiments, between about 20 and about 100 mole percent of ligands in the population of nanostructures comprise a polythiol ligand. In some embodiments, at least one organic resin is a thiol-functionalized resin.

The present invention provides a method of preparing a nanostructure composition, the method comprising:
  (a) providing a composition comprising at least one population of nanostructures, wherein between about 20 and about 100 mole percent of ligands in the population of nanostructures comprise a polythiol ligand bound to the nanostructures; and
  (b) admixing at least one organic resin with the composition of (a), wherein the at least one organic resin is soluble in a polar solvent.

In some embodiments, the population of nanostructures emits red, green, or blue light. In some embodiments, the respective portions of red, green, and blue light can be controlled to achieve a desired white point for the white light emitted by a display device incorporating a nanostructure film.

In some embodiments, the nanostructure composition comprises at least one population of nanostructure materials. In some embodiments, the nanostructure composition comprises a population of between 1 and 5, 1 and 4, 1 and 3, 1 and 2, 2 and 5, 2 and 4, 2 and 3, 3 and 5, 3 and 4, or 4 and 5 nanostructure materials. Any suitable ratio of the populations of quantum dots can be combined to create the desired nanostructure composition characteristics. In some embodiments, the nanostructure is a quantum dot.

In some embodiments, the nanostructure composition comprises at least one organic resin. In some embodiments, the nanostructure composition comprises between 1 and 5, 1 and 4, 1 and 3, 1 and 2, 2 and 5, 2 and 4, 2 and 3, 3 and 5, 3 and 4, or 4 and 5 organic resins. In some embodiments, the nanostructure composition comprises between 1 and 3, 1 and 2, or 2 and 3 organic resins. In some embodiments, the nanostructure composition comprises 1 organic resin. In some embodiments, the nanostructure is a quantum dot.

In some embodiments, the weight percentage of the population of nanostructures in the nanostructure composition is between about 0.001% and about 2%, about 0.001% and about 1%, about 0.001% and about 0.5%, about 0.001% and about 0.1%, about 0.001% and 0.01%, about 0.01% and about 2%, about 0.01% and about 1%, about 0.01% and about 0.5%, about 0.01% and about 0.1%, about 0.1% and about 2%, about 0.1% and about 1%, about 0.1% and about 0.5%, about 0.5% and about 2%, about 0.5% and about 1%, or about 1% and about 2%. In some embodiments, the nanostructure is a quantum dot.

In some embodiments, the weight percentage of the organic resin in the nanostructure composition is between about 5% and about 50%, about 5% and about 40%, about 5% and about 30%, about 5% and about 20%, about 5% and about 10%, about 10% and about 50%, about 10% and about 40%, about 10% and about 30%, about 10% and about 20%, about 20% and about 50%, about 20% and about 40%, about 20% and about 30%, about 30% and about 50%, about 30% and about 40%, or about 40% and about 50%.

In some embodiments, the at least one organic resin is admixed with the at least one population of nanostructures at an agitation rate of between about 100 rpm and about 10,000 rpm, about 100 rpm and about 5,000 rpm, about 100 rpm and about 3,000 rpm, about 100 rpm and about 1,000 rpm, about 100 rpm and about 500 rpm, about 500 rpm and about 10,000 rpm, about 500 rpm and about 5,000 rpm, about 500 rpm and about 3,000 rpm, about 500 rpm and about 1,000 rpm, about 1,000 rpm and about 10,000 rpm, about 1,000 rpm and about 5,000 rpm, about 1,000 rpm and about 3,000 rpm, about 3,000 rpm and about 10,000 rpm, about 3,000 rpm and about 10,000 rpm, or about 5,000 rpm and about 10,000 rpm.

In some embodiments, the at least one organic resin is admixed with the at least one population of nanostructures at a temperature between about −5° C. and about 100° C., about −5° C. and about 75° C., about −5° C. and about 50° C., about −5° C. and about 23° C., about 23° C. and about 100° C., about 23° C. and about 75° C., about 23° C. and about 50° C., about 50° C. and about 100° C., about 50° C. and about 75° C., or about 75° C. and about 100° C. In some embodiments, the at least one organic resin is admixed with the at least one population of nanostructures at a temperature between about 23° C. and about 50° C.

In some embodiments, the least one organic resin is admixed with the at least one population of nanostructures for a time of between about 10 minutes and about 24 hours, about 10 minutes and about 20 hours, about 10 minutes and about 15 hours, about 10 minutes and about 10 hours, about 10 minutes and about 5 hours, about 10 minutes and about 1 hour, about 10 minutes and about 30 minutes, about 30 minutes and about 24 hours, about 30 minutes and about 20 hours, about 30 minutes and about 15 hours, about 30 minutes and about 10 hours, about 30 minutes and about 5 hours, about 30 minutes and about 1 hour, about 1 hour and about 24 hours, about 1 hour and about 20 hours, about 1 hour and about 15 hours, about 1 hour and about 10 hours, about 1 hour and about 5 hours, about 5 hours and about 24 hours, about 5 hours and about 20 hours, about 5 hours and about 15 hours, about 5 hours and about 10 hours, about 10 hours and about 24 hours, about 10 hours and about 20 hours, about 10 hours and about 15 hours, about 15 hours and about 24 hours, about 15 hours and about 20 hours, or about 20 hours and about 24 hours.

In some embodiments, the admixing further comprises a solvent. In some embodiments, the solvent is selected from the group consisting of chloroform, acetone, butanone, ethylene glycol monoethyl ether, ethylene glycol monopropyl ether, ethylene glycol monobutyl ether, diethylene glycol diethyl ether, methyl ethyl ketone, methyl isobutyl ketone, monomethyl ether glycol ester, gamma-butyrolactone, methylacetic-3-ethyl ether, butyl carbitol, butyl carbitol acetate, propanediol monomethyl ether, propanediol monomethyl ether acetate, cyclohexane, toluene, xylene, isopropyl alcohol, and combinations thereof.

Increased Stability of the Nanostructure Compositions Comprising Polythiol Ligands The polythiol ligand provides increased stability to the population of nanostructures in organic resin and allows for storage of the nanostructures for extended periods of time. In some embodiments, the at least one population of nanostructures can be stored with an organic resin at a temperature between about 10° C. and about 90° C. for between about 1 minute and about 3 years, about 1 minute and about 12 months, about 1 minute and about 6 months, about 1 minute and about 3 months, about 1 minute and about 1 month, about 1 minute and about 15 days, about 1 minute and about 1 day, about 1 day and about 3 years, about 1 day and about 12 months, about 1 day and about 6 months, about 1 day and about 3 months, about 1 day and about 1 month, about 1 day and about 15 days, about 15 days and about 3 years, about 15 days and about 12 months, about 15 days and about 6 months, about 15 days and about 3 months, about 15 days and about 1 month, about 1 month and about 3 years, about 1 month and about 12 months, about 1 month and about 6 months, about 1 month and about 3 months, about 3 months and about 3 years, about 3 months and about 12 months, about 3 months and about 6 months, about 6 months and about 3 years, about 6 months and about 12 months, or about 12 months and about 3 years.

The polythiol ligand provides increased stability to the population of nanostructures in an organic resin and allows for storage of the nanostructures for extended periods of time. In some embodiments, the at least one population of nanostructures can be stored with an organic resin at a temperature between about 30° C. and about 90° C. for between about 1 minute and about 3 years, about 1 minute and about 12 months, about 1 minute and about 6 months, about 1 minute and about 3 months, about 1 minute and about 1 month, about 1 minute and about 15 days, about 1 minute and about 1 day, about 1 day and about 3 years, about 1 day and about 12 months, about 1 day and about 6 months, about 1 day and about 3 months, about 1 day and about 1 month, about 1 day and about 15 days, about 15 days and about 3 years, about 15 days and about 12 months, about 15 days and about 6 months, about 15 days and about 3 months, about 15 days and about 1 month, about 1 month and about 3 years, about 1 month and about 12 months, about 1 month and about 6 months, about 1 month and about 3 months, about 3 months and about 3 years, about 3 months and about 12 months, about 3 months and about 6 months, about 6 months and about 3 years, about 6 months and about 12 months, or about 12 months and about 3 years.

Making a Nanostructure Layer

The nanostructures used in the present invention can be embedded in a polymeric matrix using any suitable method. As used herein, the term "embedded" is used to indicate that the nanostructure population is enclosed or encased with polymer that makes up the majority of the component of the matrix. In some embodiments, at least one nanostructure population is suitably uniformly distributed throughout the matrix. In some embodiments, the at least one nanostructure population is distributed according to an application-specific distribution. In some embodiments, the nanostructures are mixed in a polymer and applied to the surface of a substrate.

The nanostructure composition can be deposited by any suitable method known in the art, including but not limited to painting, spray coating, solvent spraying, wet coating, adhesive coating, spin coating, tape-coating, roll coating, flow coating, inkjet vapor jetting, drop casting, blade coating, mist deposition, or a combination thereof. Preferably, the nanostructure composition is cured after deposition. Suitable curing methods include photo-curing, such as UV curing, and thermal curing. Traditional laminate film processing methods, tape-coating methods, and/or roll-to-roll fabrication methods can be employed in forming the nanostructure films. The nanostructure composition can be coated directly onto the desired layer of a substrate. Alternatively, the nanostructure composition can be formed into a solid layer as an independent element and subsequently applied to the substrate. In some embodiments, the nanostructure composition can be deposited on one or more barrier layers.

Spin Coating

In some embodiments, the nanostructure composition is deposited onto a substrate using spin coating. In spin coating a small amount of material is typically deposited onto the center of a substrate loaded a machine called the spinner which is secured by a vacuum. A high speed of rotation is applied on the substrate through the spinner which causes centripetal force to spread the material from the center to the edge of the substrate. While most of the material would be spun off, a certain amount remains on the substrate, forming a thin film of material on the surface as the rotation continues. The final thickness of the film is determined by the nature of the deposited material and the substrate in addition to the parameters chosen for the spin process such as spin speed, acceleration, and spin time. For typical films, a spin speed of 1500 to 6000 rpm is used with a spin time of 10-60 seconds.

Mist Deposition

In some embodiments, the nanostructure composition is deposited onto a substrate using mist deposition. Mist deposition takes place at room temperature and atmospheric pressure and allows precise control over film thickness by changing the process conditions. During mist deposition, a liquid source material is turned into a very fine mist and carried to the deposition chamber by nitrogen gas. The mist is then drawn to the wafer surface by a high voltage potential between the field screen and the wafer holder. Once the droplets coalesce on the wafer surface, the wafer is removed from the chamber and thermally cured to allow the solvent to evaporate. The liquid precursor is a mixture of solvent and material to be deposited. It is carried to the atomizer by pressurized nitrogen gas. Price, S. C., et al., "Formation of Ultra-Thin Quantum Dot Films by Mist Deposition," *ESC Transactions* 11:89-94 (2007).

Spray Coating

In some embodiments, the nanostructure composition is deposited onto a substrate using spray coating. The typical equipment for spray coating comprises a spray nozzle, an atomizer, a precursor solution, and a carrier gas. In the spray deposition process, a precursor solution is pulverized into micro sized drops by means of a carrier gas or by atomization (e.g., ultrasonic, air blast, or electrostatic). The droplets that come out of the atomizer are accelerated by the substrate surface through the nozzle by help of the carrier gas which is controlled and regulated as desired. Relative motion between the spray nozzle and the substrate is defined by design for the purpose of full coverage on the substrate.

In some embodiments, application of the nanostructure composition further comprises a solvent. In some embodiments, the solvent for application of the nanostructure composition is water, organic solvents, inorganic solvents, halogenated organic solvents, or mixtures thereof. Illustrative solvents include, but are not limited to, water, $D_2O$, acetone, ethanol, dioxane, ethyl acetate, methyl ethyl ketone, isopropanol, anisole, γ-butyrolactone, dimethylformamide, N-methylpyrroldinone, dimethylacetamide, hexamethylphosphoramide, toluene, dimethylsulfoxide, cyclopentanone, tetramethylene sulfoxide, xylene, ε-caprolactone, tetrahydrofuran, tetrachloroethylene, chloroform, chlorobenzene, dichloromethane, 1,2-dichloroethane, 1,1,2,2-tetrachloroethane, or mixtures thereof.

In some embodiments, the nanostructure compositions are thermally cured to form the nanostructure layer. In some embodiments, the compositions are cured using UV light. In some embodiments, the nanostructure composition is coated directly onto a barrier layer of a nanostructure film, and an additional barrier layer is subsequently deposited upon the nanostructure layer to create the nanostructure film. A support substrate can be employed beneath the barrier film for added strength, stability, and coating uniformity, and to prevent material inconsistency, air bubble formation, and wrinkling or folding of the barrier layer material or other materials. Additionally, one or more barrier layers are preferably deposited over a nanostructure layer to seal the material between the top and bottom barrier layers. Suitably, the barrier layers can be deposited as a laminate film and optionally sealed or further processed, followed by incorporation of the nanostructure film into the particular lighting device. The nanostructure composition deposition process can include additional or varied components, as will be understood by persons of ordinary skill in the art. Such embodiments will allow for in-line process adjustments of the nanostructure emission characteristics, such as brightness and color (e.g., to adjust the quantum dot film white point), as well as the nanostructure film thickness and other characteristics. Additionally, these embodiments will allow for periodic testing of the nanostructure film characteristics during production, as well as any necessary toggling to achieve precise nanostructure film characteristics. Such testing and adjustments can also be accomplished without changing the mechanical configuration of the processing line, as a computer program can be employed to electronically change the respective amounts of mixtures to be used in forming a nanostructure film.

Barrier Layers

In some embodiments, the nanostructure molded article comprises one or more barrier layers disposed on either one or both sides of the nanostructure layer. Suitable barrier layers protect the nanostructure layer and the nanostructure molded article from environmental conditions such as high temperatures, oxygen, and moisture. Suitable barrier materials include non-yellowing, transparent optical materials which are hydrophobic, chemically and mechanically compatible with the nanostructure molded article, exhibit photo- and chemical-stability, and can withstand high temperatures. Preferably, the one or more barrier layers are index-matched to the nanostructure molded article. In preferred embodiments, the matrix material of the nanostructure molded article and the one or more adjacent barrier layers are index-matched to have similar refractive indices, such that most of the light transmitting through the barrier layer toward the nanostructure molded article is transmitted from the barrier layer into the nanostructure layer. This index-matching reduces optical losses at the interface between the barrier and matrix materials.

The barrier layers are suitably solid materials, and can be a cured liquid, gel, or polymer. The barrier layers can comprise flexible or non-flexible materials, depending on the particular application. Barrier layers are preferably planar layers, and can include any suitable shape and surface area configuration, depending on the particular lighting application. In preferred embodiments, the one or more barrier layers will be compatible with laminate film processing techniques, whereby the nanostructure layer is disposed on at least a first barrier layer, and at least a second barrier layer is disposed on the nanostructure layer on a side opposite the nanostructure layer to form the nanostructure molded article according to one embodiment. Suitable barrier materials include any suitable barrier materials known in the art. For example, suitable barrier materials include glasses, polymers, and oxides. Suitable barrier layer materials include, but are not limited to, polymers such as polyethylene terephthalate (PET); oxides such as silicon oxide, titanium oxide, or aluminum oxide (e.g., $SiO_2$, $Si_2O_3$, $TiO_2$, or $Al_2O_3$); and suitable combinations thereof. Preferably, each barrier layer of the nanostructure molded article comprises at least 2 layers comprising different materials or compositions, such that the multi-layered barrier eliminates or reduces pinhole defect alignment in the barrier layer, providing an effective barrier to oxygen and moisture penetration into the nanostructure layer. The nanostructure layer can include any suitable material or combination of materials and any suitable number of barrier layers on either or both sides of the nanostructure layer. The materials, thickness, and number of barrier layers will depend on the particular application, and will suitably be chosen to maximize barrier protection and brightness of the nanostructure layer while minimizing thickness of the nanostructure molded article. In preferred embodiments, each barrier layer comprises a laminate film, preferably a dual laminate film, wherein the thickness of each barrier layer is sufficiently thick to eliminate wrinkling in roll-to-roll or laminate manufacturing processes. The number or thickness of the barriers may further depend on legal toxicity guidelines in embodiments where the nanostructures comprise heavy metals or other toxic materials, which guidelines may require more or thicker barrier layers. Additional considerations for the barriers include cost, availability, and mechanical strength.

In some embodiments, the nanostructure film comprises two or more barrier layers adjacent each side of the nanostructure layer, for example, two or three layers on each side or two barrier layers on each side of the nanostructure layer. In some embodiments, each barrier layer comprises a thin glass sheet, e.g., glass sheets having a thickness of about 100 µm, 100 µm or less, or 50 µm or less.

Each barrier layer of the nanostructure film can have any suitable thickness, which will depend on the particular requirements and characteristics of the lighting device and application, as well as the individual film components such as the barrier layers and the nanostructure layer, as will be understood by persons of ordinary skill in the art. In some embodiments, each barrier layer can have a thickness of 50 µm or less, 40 µm or less, 30 µm or less, 25 µm or less, 20 µm or less, or 15 µm or less. In certain embodiments, the barrier layer comprises an oxide coating, which can comprise materials such as silicon oxide, titanium oxide, and aluminum oxide (e.g., $SiO_2$, $Si_2O_3$, $TiO_2$, or $Al_2O_3$). The oxide coating can have a thickness of about 10 µm or less, 5 µm or less, 1 µm or less, or 100 nm or less. In certain embodiments, the barrier comprises a thin oxide coating with a thickness of about 100 nm or less, 10 nm or less, 5 nm or less, or 3 nm or less. The top and/or bottom barrier can consist of the thin oxide coating, or may comprise the thin oxide coating and one or more additional material layers.

Improved Properties of the Nanostructure Films

Films prepared using nanostructure compositions comprising a population of nanostructures comprising polythiol ligands in an organic resin provide increased stability at high temperatures. In some embodiments, films prepared using the nanostructure compositions can be stably stored at a temperature between 40° C. and 100° C. for between about 1 minute and about 3 years, about 1 minute and about 12 months, about 1 minute and about 6 months, about 1 minute and about 3 months, about 1 minute and about 1 month, about 1 minute and about 15 days, about 1 minute and about 1 day, about 1 day and about 3 years, about 1 day and about 12 months, about 1 day and about 6 months, about 1 day and about 3 months, about 1 day and about 1 month, about 1 day and about 15 days, about 15 days and about 3 years, about 15 days and about 12 months, about 15 days and about 6 months, about 15 days and about 3 months, about 15 days and about 1 month, about 1 month and about 3 years, about 1 month and about 12 months, about 1 month and about 6 months, about 1 month and about 3 months, about 3 months and about 3 years, about 3 months and about 12 months, about 3 months and about 6 months, about 6 months and about 3 years, about 6 months and about 12 months, or about 12 months and about 3 years.

Films prepared using nanostructure compositions comprising a population of nanostructures comprising polythiol ligands in an organic resin provide increased stability at high humidity levels. In some embodiments, films prepared using the nanostructure compositions can be stably stored at a relative humidity level between about 60% and about 100% for between about 1 minute and about 3 years, about 1 minute and about 12 months, about 1 minute and about 6 months, about 1 minute and about 3 months, about 1 minute and about 1 month, about 1 minute and about 15 days, about 1 minute and about 1 day, about 1 day and about 3 years, about 1 day and about 12 months, about 1 day and about 6 months, about 1 day and about 3 months, about 1 day and about 1 month, about 1 day and about 15 days, about 15 days and about 3 years, about 15 days and about 12 months, about 15 days and about 6 months, about 15 days and about 3 months, about 15 days and about 1 month, about 1 month and about 3 years, about 1 month and about 12 months, about 1 month and about 6 months, about 1 month and about 3 months, about 3 months and about 3 years, about 3 months and about 12 months, about 3 months and about 6 months, about 6 months and about 3 years, about 6 months and about 12 months, or about 12 months and about 3 years.

Films prepared using nanostructure compositions comprising a population of nanostructures comprising polythiol ligands in an organic resin provide increased light conversion efficiency (LCE). In some embodiments, films prepared using the nanostructure compositions display a light conversion efficiency of between about 20% and about 40%, about 20% and about 30%, about 20% and about 25%, about 20% and about 22.5%, about 22.5% and about 40%, about 22.5% and about 30%, about 22.5% and about 25%, about 25% and about 40%, about 25% and about 30%, or about 30% and about 40%. In some embodiments, films prepared using the nanostructure composition display a color conversion efficiency between about 20% and about 25%.

Nanostructure Film Features and Embodiments

In some embodiments, the nanostructure films are used to form display devices. As used herein, a display device refers to any system with a lighting display. Such devices include, but are not limited to, devices encompassing a liquid crystal display (LCD), televisions, computers, mobile phones, smart phones, personal digital assistants (PDAs), gaming devices, electronic reading devices, digital cameras, and the like.

EXAMPLES

The following examples are illustrative and non-limiting, of the products and methods described herein. Suitable modifications and adaptations of the variety of conditions, formulations, and other parameters normally encountered in the field and which are obvious to those skilled in the art in view of this disclosure are within the spirit and scope of the invention.

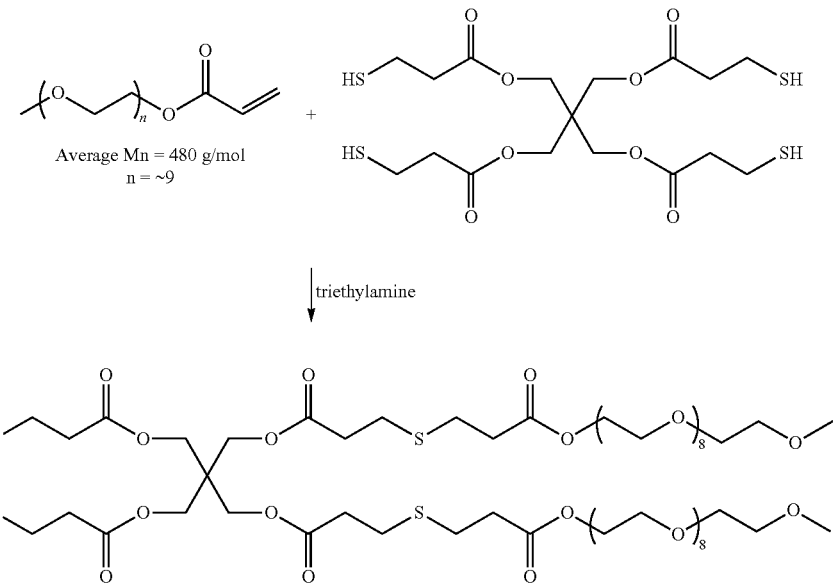

Example 1

Synthesis of PETMP-PEG480

A 78.582 g solution of poly(ethylene glycol) methyl ether acrylate (average Mn 480 (Sigma Aldrich, St. Louis, MO)) (PEG480) and 1.092 mL of trimethylamine (TEA) were added to a round bottom flask at room temperature and stirred for 5 minutes until homogeneous. To the solution was added 80 g of pentaerythritol tetrakis(3-mercaptopropionate (Evans Chemetics L P, Waterloo, NY) (PETMP) and the mixture was stirred at room temperature for 30 minutes. Due to the exothermic nature of the reaction, the temperature rose to about 40° C. The flask was further heated at 80° C. for 1.5 hours. The flask was then cooled to 60° C. and TEA was removed by applying vacuum (100 mTorr) for 2 hours. The final product was characterized by FTIR and $H^1$—NMR where consumption of the C=C—H stretch and proton signals were confirmed.

Example 2

Ligand Exchange with PETMP-PEG480 Ligands

To a 100 mL round bottom flask was added 6.0 mL of quantum dots in heptane, 0.379 g of PETMP-PEG-480, and 12.0 mL of degassed polypropylene glycol methyl ether acetate (PGMEA) under nitrogen. The flask was heated to 80° C. for 1 hour with agitation. The hazy solution cleared during the ligand exchange. The solution was cooled to room temperature, then 36 mL of degassed heptane (4×total ligand exchange solution volume) was added in a TEFLON centrifuge bottle to precipitate the quantum dots comprising bound PETMP-PEG-480 ligands. The cloudy suspension of quantum dots comprising bound PETMP-PEG-480 ligands was centrifuged for 15 minutes at 4000 rpm to yield a pellet and a clear supernatant phase. The supernatant was discarded and the quantum dots comprising bound PETMP-PEG-480 ligands was redispersed in 0.948 mL of degassed PGMEA with stirring. Before ligand exchange, the quantum dots were not soluble in PGMEA.

Example 3

Ligand Exchange with PEG1000-CA Ligands

Quantum dots comprising bound carboxylic acid-terminated PEG-1000 (PEG-1000-CA) ligands were prepared using the method of Example 2 and substituting PETMP-PEG480 with PEG1000-CA. The carboxylic acid-terminated PEG-1000 ligands were prepared using the method described in Int'l. Patent Appl. Publication No. WO 2019/084119, which is incorporated herein by reference in its entirety.

Example 4

Quantum Yield Results for Different Ratios of PETMP-PEG480 or PEG1000-CA

Quantum dots comprising bound PETMP-PEG-480 ligands and quantum dots comprising bound PEG-1000-CA were prepared using different concentration ratios of ligands to quantum dots. The concentration (mg/mL) of the ligands and the concentration of the quantum dots were determined by measuring the optical density (OD) of the ligand dispersion or quantum dot dispersion with a UV-VIS spectrometer at a wavelength of 450 nm. From the individual concentration measurements, the ratio of ligands to quantum dots was measured using the formula:

Ligand/Quantum Dot Ratio=$OD_{450}$ ligands/$OD_{450}$ quantum dots

Quantum yield measurements for the quantum dots comprising bound PETMP-PEG-480 at three different ligand/quantum dot ratios and for quantum dots comprising bound PEG-1000-CA are shown in TABLE 1.

TABLE 1

| Ligand | Ligand/Quantum Dot Ratio | Quantum Yield |
|---|---|---|
| PETMP-PEG-480 | 1 | 87.4% |
| PETMP-PEG-480 | 2.5 | 85.2% |
| PETMP-PEG-480 | 5 | 83.9% |
| PEG-1000-CA | 1 | 87.0% |

As shown in TABLE 1, quantum dots comprising bound PETMP-PEG-480 ligands in a ratio of 1 provided a quantum yield of 87.4% and decreased with increasing ratio of ligands/quantum dots with quantum dots comprising bound PETMP-PEG-480 ligands providing a quantum yield of 83.9%. The quantum yield obtained with the quantum dots comprising bound PETMP-PEG-480 ligands were comparable to those obtained with quantum dots comprising bound PEG-1000-CA ligands having the same ligand/quantum dot ratio.

Example 5

Preparation of Quantum Dot Films

A solution of quantum dots comprising bound PETMP-PEG-480 ligands (or PEG-1000-CA ligands) in PGMEA was added to a polymer formulation (also dissolved in PGMEA). The solution was processed into a film by solvent evaporation at 100° C. followed by thermal curing at 180° C. As shown in TABLE 2, films prepared using quantum dots comprising bound PETMP-PEG-480 ligands showed improved brightness over films prepared using quantum dots comprising bound PEG-1000-CA ligands. Brightness of the quantum dots films is a measurement of the light conversion efficiency (LCE).

TABLE 2

| Ligand | Ligand/Quantum Dot Ratio (mg/OD) | Film Brightness (LCE) |
|---|---|---|
| PETMP-PEG-480 | 1 | 23.9% |
| PETMP-PEG-480 | 2.5 | 24.0% |
| PETMP-PEG-480 | 5 | 24.1% |
| PEG-1000-CA | 1 | 22.5% |

Example 6

Weight Loss of the Quantum Dot Films After Thermal Heating

The weight of quantum dots comprising bound PETMP-PEG-480 ligands and quantum dots comprising bound PEG-1000-CA ligands were measured before and after thermal curing at 180° C. for 30 minutes. Results are shown in TABLE 3.

TABLE 3

| Ligand | Ligand/Quantum Dot Ratio (mg/OD) | Weight Loss |
|---|---|---|
| PETMP-PEG-480 | 1 | 2.0% |
| PEG-1000-CA | 1 | 23.1% |

As shown in TABLE 3, quantum dots comprising bound PETMP-PEG-480 ligands are much more thermally stable than quantum dots comprising bound PEG-1000-CA ligands. It is believed that the increased thermal stability contributes to the improved film brightness of the quantum dots comprising bound PETMP-PEG-480 ligands.

Example 7

QDCF (Quantum Dot Color Filter) Formulation Example

Formulations for QDCF applications are prepared by combining the QD solution with other components used in inks. Examples are shown in TABLE 4.

TABLE 4

| Ink type | Ink components | QD solvent |
|---|---|---|
| Solvent-based | Quantum dots, reactive polymers, curing agents, scattering particles, solvent | Propylene glycol methyl ether acetate (PGMEA) |
| Solvent-free | Quantum dots, monomers, photo (or thermal) initiators, scattering particles, dispersant | Hexanediol dimethacrylate or other monomer |

Films may be deposited by spin-coating the above formulations at three different speeds (for example, 200, 400, and 600 rpm) on 2"×2" pre-cleaned glass substrates. Depending on the ink type, the films may be cured by heating (20-40 minutes at 150° C. in $N_2$) or irradiating with UV light (1000-2000 $mJ/cm^2$).

The films may be transferred to an optical platform to measure the blue transmission and photon conversion efficiency (PCE). Film thickness may be measured using a profilometer.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A nanostructure composition comprising:
   (a) a nanostructure; and
   (b) polythiol ligands dispersed on the surface of the nanostructure, the polythiol ligands having the formula I:

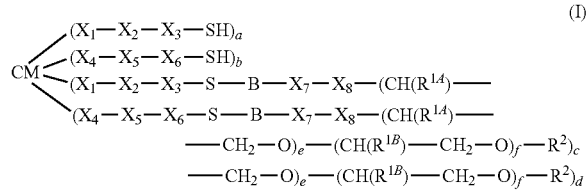

wherein:
CM is a central moiety, wherein CM is selected from the group consisting of an alkane, a 1,3,5-triazine, a pentaerythritol, a 1,3,5-triazine-2,4,6-trione, a trimethylolpropane, and a (propane-2,2-diylbis(4,1-phenylene)) bis(λ'-oxy);
$X_1$ is a bond, —C(═O)—, a $C_{1-10}$ alkylene, or a $C_{2-10}$ heteroalkylene;
$X_2$ is a bond, —C(═O)—, a $C_{1-10}$ alkylene, or a $C_{2-10}$ heteroalkylene;
$X_3$ is a bond, —C(═O)—, a $C_{1-10}$ alkylene, or a $C_{2-10}$ heteroalkylene;
$X_4$ is a bond, —C(═O)—, a $C_{1-10}$ alkylene, or a $C_{2-10}$ heteroalkylene;
$X_5$ is a bond, —C(═O)—, a $C_{1-10}$ alkylene, or a $C_{2-10}$ heteroalkylene;
$X_6$ is a bond, —C(═O)—, a $C_{1-10}$ alkylene, or a $C_{2-10}$ heteroalkylene;
B is —$CH_2$—$CH_2$—C(═O)—O—, —$CH_2$—C($CH_3$)$_2$—C(═O)—O—, —$CH_2$—CH($CH_3$)—C(═O)—NH—, —C(═O)—NH—, —$CH_2$—$CH_2$—, or —$CH_2$—CH(OH)—$CH_2$—O—;
$X_7$ is a bond or $C_{1-12}$ alkylene;
$X_8$ is a bond, —O—, —C(═O)—O—, or —C(═O)—N—;
$R^{1A}$ and $R^{1B}$ independently are H or $C_{1-20}$ alkyl;
$R^2$ is $C_{1-20}$ alkyl or $C_{1-20}$ alkoxy;
a is 2 to 10;
b is 0 to 10;
c is 2 to 10;
d is 0 to 10;
e is 1 to 100; and
f is 0 to 100;
wherein a+b+c+d has a value within a range of 4 to 40.

2. The nanostructure composition of claim 1, wherein the polythiol ligands have formula II:

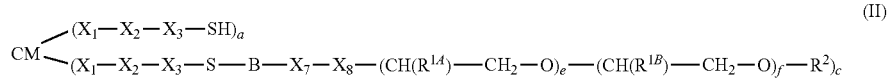

wherein:
CM is a central moiety;
$X_1$ is a bond, —C(═O)—, a $C_{1-10}$ alkylene, or a $C_{2-10}$ heteroalkylene;
$X_2$ is a bond, —C(═O)—, a $C_{1-10}$ alkylene, or a $C_{2-10}$ heteroalkylene;
$X_3$ is a bond, —C(═O)—, a $C_{1-10}$ alkylene, or a $C_{2-10}$ heteroalkylene;
B is —$CH_2$—$CH_2$—C(═O)—O—, —$CH_2$—C($CH_3$)$_2$—C(═O)—O—, —$CH_2$—CH($CH_3$)—C(═O)—NH—, —C(═O)—NH—, —$CH_2$—$CH_2$—, or —$CH_2$—CH(OH)—$CH_2$—O—;
$X_7$ is a bond or $C_{1-12}$ alkylene;
$X_8$ is a bond, —O—, —C(═O)—O—, or —C(═O)—N—;
$R^{1A}$ and $R^{1B}$ independently are H or $C_{1-20}$ alkylene;
$R^2$ is $C_{1-20}$ alkylene or $C_{1-20}$ alkoxy;
a is 2 to 10;
c is 2 to 10;
e is 1 to 100; and
f is 0 to 100;
wherein a +c ≥4 and ≤20.

3. The nanostructure composition of claim 1, wherein the nanostructure comprises a core selected from the group consisting of InP, InZnP, InGaP, CdSe, CdS, CdSSe, CdZnSe, CdZnS, ZnSe, ZnSSe, InAs, InGaAs, and InAsP.

4. The nanostructure composition of claim 1, wherein the nanostructure comprises at least one shell.

5. The nanostructure composition of claim 1, wherein $X_1$, $X_2$, and $X_3$ are a bond.

6. The nanostructure composition of claim 1, wherein $X_1$ is —C(═O)—, $X_2$ is a $C_{1-10}$ alkylene, and $X_3$ is a bond.

7. The nanostructure composition of claim 1, wherein $X_1$ is $C_{2-10}$ heteroalkylene, $X_2$ is —C(═O)—, and $X_3$ is a $C_{1-10}$ alkylene.

8. The nanostructure composition of claim 1, wherein $X_1$ is a substituted $C_{2-10}$ heteroalkylene, $X_2$ is a bond, and $X_3$ is a bond.

9. The nanostructure composition of claim 1, wherein B is —$CH_2$—$CH_2$—.

10. The nanostructure composition of claim 1, wherein $X_7$ is a $C_{1-10}$ alkylene and $X_8$ is —C(=O)—O—.

11. The nanostructure composition of claim 1, wherein $R^{1A}$ is H, e is 1 to 100, a is 2, and c is 2.

12. The nanostructure composition of claim 1, wherein the nanostructure composition is soluble in a solvent selected from the group consisting of water, methanol, ethanol, acetone, methyl ethyl ketone, isopropanol, n-propanol, acetonitrile, dimethyl sulfoxide, dimethyl formamide, ethylene glycol, diethylene glycol, benzonitrile, cyclohexane, chloroform, ethyl acetate, propylene glycol methyl acetate, and dichloromethane.

13. A method of replacing a first ligand on a nanostructure with a second ligand comprising admixing a reaction mixture comprising a population of nanostructures having a first ligand non-covalently bound to the nanostructure and a second ligand which is a polythiol ligand, such that the second ligand displaces the first ligand and becomes non-covalently bound to the nanostructure, wherein the polythiol ligand has formula I:

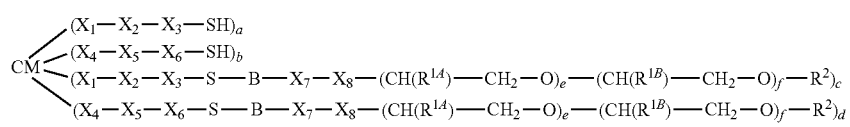

(I)

wherein:
CM is a central moiety, wherein CM is selected from the group consisting of an alkane, a 1,3,5-triazine, a pentaerythritol, a 1,3,5-triazine-2,4,6-trione, a trimethylolpropane, and a (propane-2,2-diylbis(4,1-phenylene))bis(λ'-oxy);

$X_1$ is a bond, —C(=O)—, a $C_{1-10}$ alkylene, or a $C_{2-10}$ heteroalkylene;

$X_2$ is a bond, —C(=O)—, a $C_{1-10}$ alkylene, or a $C_{2-10}$ heteroalkylene;

$X_3$ is a bond, —C(=O)—, a $C_{1-10}$ alkylene, or a $C_{2-10}$ heteroalkylene;

$X_4$ is a bond, —C(=O)—, a $C_{1-10}$ alkylene, or a $C_{2-10}$ heteroalkylene;

$X_5$ is a bond, —C(=O)—, a $C_{1-10}$ alkylene, or a $C_{2-10}$ heteroalkylene;

$X_6$ is a bond, —C(=O)—, a $C_{1-10}$ alkylene, or a $C_{2-10}$ heteroalkylene;

B is —$CH_2$—$CH_2$—C(=O)—O—, —$CH_2$—C($CH_3$)$_2$—C(=O)—O—, —$CH_2$—CH($CH_3$)—C(=O)—NH—, —C(=O)—NH—, —$CH_2$—$CH_2$—, or —$CH_2$—CH(OH)—$CH_2$—O—;

$X_7$ is a bond or $C_{1-12}$ alkylene;

$X_8$ is a bond, —O—, —C(=O)—O—, or —C(=O)—N—;

$R^{1A}$ and $R^{1B}$ independently are H or $C_{1-20}$ alkyl;

$R^2$ is $C_{1-20}$ alkyl or $C_{1-20}$ alkoxy;

a is 2 to 10;
b is 0 to 10;
c is 2 to 10;
d is 0 to 10;
e is 1 to 100; and
f is 0 to 100;

wherein a+b+c+d has a value within a range of 4 to 40.

14. The method of claim 13, wherein the nanostructure comprises a core selected from the group consisting of InP, InZnP, InGaP, CdSe, CdS, CdSSe, CdZnSe, CdZnS, ZnSe, ZnSSe, InAs, InGaAs, and InAsP.

15. A nanostructure film layer comprising:
(a) a nanostructure;
(b) polythiol ligands dispersed on the surface of the nanostructure, the polythiol ligands having the formula I:

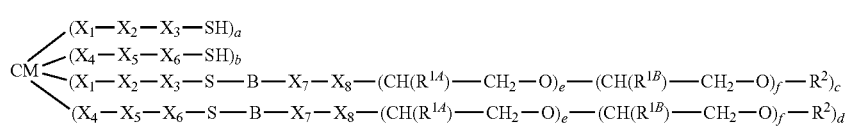
(I)

wherein:
- CM is a central moiety, wherein CM is selected from the group consisting of an alkane, a 1,3,5-triazine, a pentaerythritol, a 1,3,5-triazine-2,4,6-trione, a trimethylolpropane, and a (propane-2,2-diylbis(4,1-phenylene)) bis(λ'-oxy);
- $X_1$ is a bond, —C(=O)—, a $C_{1-10}$ alkylene, or a $C_{2-10}$ heteroalkylene;
- $X_2$ is a bond, —C(=O)—, a $C_{1-10}$ alkylene, or a $C_{2-10}$ heteroalkylene;
- $X_3$ is a bond, —C(=O)—, a $C_{1-10}$ alkylene, or a $C_{2-10}$ heteroalkylene;
- $X_4$ is a bond, —C(=O)—, a $C_{1-10}$ alkylene, or a $C_{2-10}$ heteroalkylene;
- $X_5$ is a bond, —C(=O)—, a $C_{1-10}$ alkylene, or a $C_{2-10}$ heteroalkylene;
- $X_6$ is a bond, —C(=O)—, a $C_{1-10}$ alkylene, or a $C_{2-10}$ heteroalkylene;
- B is —CH$_2$—CH$_2$—C(=O)—O—, —CH$_2$—C(CH$_3$)$_2$—C(=O)—O—, —CH$_2$—CH(CH$_3$)—C(=O)—NH—, —C(=O)—NH—, —CH$_2$—CH$_2$—, or —CH$_2$—CH(OH)—CH$_2$—O—;
- $X_7$ is a bond or $C_{1-12}$ alkylene;
- $X_8$ is a bond, —O—, —C(=O)—O—, or —C(=O)—N—;
- $R^{1A}$ and $R^{1B}$ independently are H or $C_{1-20}$ alkyl;
- $R^2$ is $C_{1-20}$ alkyl or $C_{1-20}$ alkoxy;
- a is 2 to 10;
- b is 0 to 10;
- c is 2 to 10;
- d is 0 to 10;
- e is 1 to 100; and
- f is 0 to 100;
wherein a+b+c+has a value within a range of 4 to 40; and
(c) at least one organic resin.

16. The nanostructure film layer of claim 15, wherein the nanostructure film layer displays a light conversion efficiency between about 20% and about 40%.

* * * * *